(12) United States Patent
Price et al.

(10) Patent No.: US 8,293,763 B2
(45) Date of Patent: Oct. 23, 2012

(54) 8-ANILINOIMIDAZOPYRIDINES AND THEIR USE AS ANTI-CANCER AND/OR ANTI-INFLAMMATORY AGENTS

(75) Inventors: Stephen Price, Harlow (GB); Robert Heald, Harlow (GB); Pascal Pierre Alexandre Savy, Harlow (GB)

(73) Assignee: Genentech, Inc., South San Francisco, CA (US)

(*) Notice: Subject to any disclaimer, the term of this patent is extended or adjusted under 35 U.S.C. 154(b) by 274 days.

(21) Appl. No.: 12/808,346

(22) PCT Filed: Dec. 18, 2008

(86) PCT No.: PCT/US2008/087476
§ 371 (c)(1),
(2), (4) Date: Jun. 29, 2010

(87) PCT Pub. No.: WO2009/085980
PCT Pub. Date: Jul. 9, 2009

(65) Prior Publication Data
US 2010/0280063 A1    Nov. 4, 2010

Related U.S. Application Data

(60) Provisional application No. 61/015,155, filed on Dec. 19, 2007, provisional application No. 61/054,024, filed on May 16, 2008.

(51) Int. Cl.
*A61K 31/437* (2006.01)
*C07D 471/04* (2006.01)
*A61P 35/00* (2006.01)
(52) U.S. Cl. ........................ 514/300; 546/121
(58) Field of Classification Search ............ 546/121; 514/300
See application file for complete search history.

(56) References Cited

FOREIGN PATENT DOCUMENTS

| WO | WO 01/05390 A2 | 1/2001 |
|---|---|---|
| WO | WO 02/06213 A2 | 1/2002 |
| WO | WO 03/077855 A1 | 9/2003 |
| WO | WO 03/077914 A1 | 9/2003 |
| WO | 2004046133 * | 6/2004 |

OTHER PUBLICATIONS

Potts et al., Journal of Heterocyclic Chemistry, (1970), vol. 7(5), pp. 1019-1027.*
Ahn et al., "Pharmacologic inhibitors of MKK1 and MKK2" *Methods in Enzymology* 332:417-431 (2001).
Davies et al., "Mutations of the BRAF gene in human cancer" *Nature* 417:949-54 (Jun. 27, 2002).
Hoshino et al., "Constitutive activation of the 41-/43-kDa mitogen-activated protein kinase signaling pathway in human tumors" *Oncogene* 18:813-822 (1999).
J.A. Spicer, "New small-molecule inhibitors of mitogen-activated protein kinase kinase" *Expert Opinion Drug Discovery* 3(7):801-817 (2008).
Khokhlatchev et al., "Phosphorylation of the MAP kinase ERK2 promotes its homodimerization and nuclear translocation" *Cell* 93:605-615 (1998).
Kohl et al., "Selective inhibition of ras-dependent transformation by a farnesyltransferase inhibitors" *Science* 260:1834-1837 (1993).
Lewis et al., "Signal transduction through MAP kinase cascades" *Adv Cancer Res.* 74:49-139 (1998).
Milella et al., "Therapeutic targeting of the MEK/MAPK signal transduction module in acute myeloid leukemia" *J. Clin. Invest.* 108(6):851-859 (2001).
Price, B., "Putative allosteric MEK1 and MEK2 inhibitors" *Expert Opin. Ther. Patents* 18(6):603-627 (2008).
Sebolt-Leopold et al., "Blockade of the MAP kinase pathway suppresses growth of colon tumors in vivo" *Nature Medicine* 5(7):810-816 (Jul. 1999).
Trachet et al., "In vivo micro-CT of mouse lungs without respiratory gating" *AACR* (Poster #5426, April 46-10, 2002).
Wallace et al., "Progress towards therapeutic small molecule MEK inhibitors for use in cancer therapy" *Current Topic in Medicinal Chem.* 5(215-229) (2005).

* cited by examiner

*Primary Examiner* — D M Seaman
*Assistant Examiner* — Niloofar Rahmani
(74) *Attorney, Agent, or Firm* — Brian L. Buckwalter

(57) ABSTRACT

The invention relates to imidazopyridines of formula I with anti-cancer and/or anti-inflammatory activity and more specifically to imidazopyridines which inhibit MEK kinase activity. The invention provides compositions and methods useful for inhibiting abnormal cell growth or treating a hyperproliferative disorder, or treating an inflammatory disease in a mammal. The invention also relates to methods of using the compounds for in vitro, in situ, and in vivo diagnosis or treatment of mammalian cells, or associated pathological conditions.(Formula I)

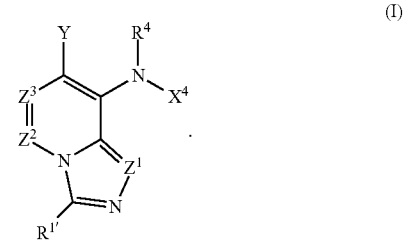

17 Claims, No Drawings

8-ANILINOIMIDAZOPYRIDINES AND THEIR USE AS ANTI-CANCER AND/OR ANTI-INFLAMMATORY AGENTS

CROSS REFERENCE TO RELATED APPLICATIONS

This application claims the benefit of U.S. provisional application number 61/015,155 filed Dec. 19, 2007 and U.S. provisional application No. 61/054,024 filed May 16, 2008, the disclosures of which are incorporated herein by reference in their entirety.

FIELD OF THE INVENTION

The invention relates to imidazopyridines with anti-cancer activity and more specifically to imidazopyridines which inhibit MEK kinase activity. The invention also relates to methods of using the compounds for in vitro, in situ, and in vivo diagnosis or treatment of mammalian cells, or associated pathological conditions.

BACKGROUND OF THE INVENTION

In the quest to understand how Ras transmits extracellular growth signals, the MAP (mitogen-activated protein) kinase (MAPK) pathway has emerged as the crucial route between membrane-bound Ras and the nucleus. The MAPK pathway encompasses a cascade of phosphorylation events involving three key kinases, namely Raf, MEK (MAP kinase kinase) and ERK (MAP kinase). Active GTP-bound Ras results in the activation and indirect phosphorylation of Raf kinase. Raf then phosphorylates MEK1 and 2 on two serine residues (S218 and S222 for MEK1 and S222 and S226 for MEK2) (Ahn et al., *Methods in Enzymology* 2001, 332, 417-431). Activated MEK then phosphorylates its only known substrates, the MAP kinases, ERK1 and 2. ERK phosphorylation by MEK occurs on Y204 and T202 for ERK1 and Y185 and T183 for ERK2 (Ahn et al., *Methods in Enzymology* 2001, 332, 417-431). Phosphorylated ERK dimerizes and then translocates to the nucleus where it accumulates (Khokhlatchev et al., *Cell* 1998, 93, 605-615). In the nucleus, ERK is involved in several important cellular functions, including but not limited to nuclear transport, signal transduction, DNA repair, nucleosome assembly and translocation, and mRNA processing and translation (Ahn et al., *Molecular Cell* 2000, 6, 1343-1354). Overall, treatment of cells with growth factors leads to the activation of ERK1 and 2 which results in proliferation and, in some cases, differentiation (Lewis et al., Adv. Cancer Res. 1998, 74, 49-139).

There has been strong evidence that genetic mutations and/or overexpression of protein kinases involved in the MAP kinase pathway lead to uncontrolled cell proliferation and, eventually, tumor formation, in proliferative diseases. For example, some cancers contain mutations which result in the continuous activation of this pathway due to continuous production of growth factors. Other mutations can lead to defects in the deactivation of the activated GTP-bound Ras complex, again resulting in activation of the MAP kinase pathway. Mutated, oncogenic forms of Ras are found in 50% of colon and >90% pancreatic cancers as well as many others types of cancers (Kohl et al., *Science* 1993, 260, 1834-1837). Recently, bRaf mutations have been identified in more than 60% of malignant melanoma (Davies, H. et al., *Nature* 2002, 417, 949-954). These mutations in bRaf result in a constitutively active MAP kinase cascade. Studies of primary tumor samples and cell lines have also shown constitutive or over-activation of the MAP kinase pathway in cancers of pancreas, colon, lung, ovary and kidney (Hoshino, R. et al., *Oncogene* 1999, 18, 813-822).

MEK has emerged as an attractive therapeutic target in the MAP kinase cascade pathway. MEK, downstream of Ras and Raf, is highly specific for the phosphorylation of MAP kinase; in fact, the only known substrates for MEK phosphorylation are the MAP kinases, ERK1 and 2 Inhibition of MEK has been shown to have potential therapeutic benefit in several studies. For example, small molecule MEK inhibitors have been shown to inhibit human tumor growth in nude mouse xenografts, (Sebolt-Leopold et al., *Nature-Medicine* 1999, 5 (7), 810-816); Trachet et al., AACR Apr. 6-10, 2002, Poster #5426; Tecle, H. IBC 2.sup.nd International Conference of Protein Kinases, Sep. 9-10, 2002), block static allodynia in animals (WO 01/05390 published Jan. 25, 2001) and inhibit growth of acute myeloid leukemia cells (Milella et al., *J Clin Invest* 2001, 108 (6), 851-859).

Several small molecule MEK inhibitors have also been discussed in, for example, WO02/06213, WO 03/077855 and WO03/077914. There still exists a need for new MEK inhibitors as effective and safe therapeutics for treating a variety of proliferative disease states, such as conditions related to the hyperactivity of MEK, as well as diseases modulated by the MEK cascade.

SUMMARY OF THE INVENTION

The invention relates generally to imidazopyridines of formula I (and/or solvates, hydrates and/or salts thereof) with anti-cancer and/or anti-inflammatory activity, and more specifically with MEK kinase inhibitory activity. Certain hyperproliferative and inflammatory disorders are characterized by the modulation of MEK kinase function, for example by mutations or overexpression of the proteins. Accordingly, the compounds of the invention and compositions thereof are useful in the treatment of hyperproliferative disorders such as cancer and/or inflammatory diseases such as rheumatoid arthritis.

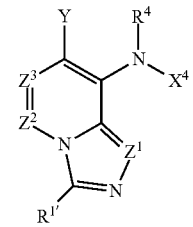

I and salts thereof, wherein:

$Z^1$ is $CR^1$ or N;

$R^1$ is H, $C_1$-$C_3$ alkyl, halo, $CF_3$, $CHF_2$, CN, $OR^A$ or $NR^AR^A$;

$R^{1'}$ is H, $C_1$-$C_3$ alkyl, halo, $CF_3$, $CHF_2$, CN, $OR^A$, or $NR^AR^A$;

wherein each $R^A$ is independently H or $C_1$-$C_3$ alkyl;

$Z^2$ is $CR^2$ or N;

$Z^3$ is $CR^3$ or N; provided that only one of $Z^1$, $Z^2$ and $Z^3$ can be N at the same time;

$R^2$ and $R^3$ are independently selected from H, halo, CN, $CF_3$, $-OCF_3$, $-NO_2$, $-(CR^{14}R^{15})_nC(=Y')R^{11}$, $-(CR^{14}R^{15})_nC(=Y')OR^{11}$, $-(CR^{14}R^{15})_nC(=Y')NR^{11}R^{12}$, $-(CR^{14}R^{15})_nNR^{11}R^{12}$, $-(CR^{14}R^{15})_nOR^{11}$, $-(CR^{14}R^{15})_nNR^{12}C(=Y')R^{11}$, $-(CR^{14}R^{15})_nNR^{12}C(=Y')OR^{11}$, $-(CR^{14}R^{15})_nNR^{13}C(=Y')NR^{11}R^{12}$, $-(CR^{14}R^{15})_n$ $NR^{12}SO_2R^{11}$, $-(CR^{14}R^{15})_nOC(=Y')R^{11}$, $-(CR^{14}R^{15})_n OC(=Y')OR^{11}$, $-(CR^{14}R^{15})_nOC(=Y')NR^{11}R^{12}$, $-(CR^{14}R^{15})_nOS(O)_2(OR^{11})$, $-(CR^{14}R^{15})_n OP(=Y')(OR^{11})(OR^{12})$, $-(CR^{14}R^{15})_nOP(OR^{11})(OR^{12})$, $-(CR^{14}R^{15})_nS(O)R^{11}$, $-(CR^{14}R^{15})_n S(O)_2R^{11}$, $-(CR^{14}R^{15})_nS(O)_2NR^{11}R^{12}$, $-(CR^{14}R^{15})_nS(O)(OR^{11})$, $-(CR^{14}R^{15})_nS(O)_2(OR^{11})$, $-(CR^{14}R^{15})_nSC(=Y')R^{11}$, $-(CR^{14}R^{15})_nSC(=Y')OR^{11}$, $-(CR^{14}R^{15})_nSC(=Y') NR^{11}R^{12}$, $C_1$-$C_{12}$ alkyl, $C_2$-$C_8$ alkenyl, $C_2$-$C_8$ alkynyl, carbocyclyl, heterocyclyl, aryl, and heteroaryl;

$R^4$ is H, $C_1$-$C_6$ alkyl or $C_3$-$C_4$ carbocyclyl;

Y is W—C(O)— or W';

W is

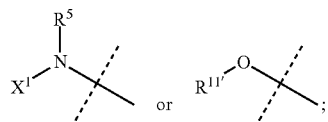

$R^5$ is H or $C_1$-$C_{12}$ alkyl;

$X^1$ is selected from $R^{11'}$ and $-OR^{11'}$; when $X^1$ is $R^{11'}$, $X^1$ is optionally taken together with $R^5$ and the nitrogen atom to which they are bound to form a 4-7 membered saturated or unsaturated ring having 0-2 additional heteroatoms selected from O, S and N, wherein said ring is optionally substituted with one or more groups selected from halo, CN, $CF_3$, $-OCF_3$, $-NO_2$, oxo, $-(CR^{19}R^{20})_nC(=Y')R^{16}$, $-(CR^{19}R^{20})_nC(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_n-SR^{16}$, $-(CR^{19}R^{20})_nNR^{16}C(=Y')R^{17}$, $-(CR^{19}R^{20})_nNR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_n OC(=Y')R^{16}$, $-(CR^{19}R^{20})_nOC(=Y')OR^{16}$, $-(CR^{19}R^{20})_n OC(=Y')NR^{16}R^{17}$, $-(CR^{19}R^{20})_nOS(O)_2(OR^{16})$, $-(CR^{19}R^{20})_nOP(=Y')(OR^{16})(OR^{17})$, $-(CR^{19}R^{20})_nOP (OR^{16})(OR^{17})$, $-(CR^{19}R^{20})_nS(O)R^{16}$, $-(CR^{19}R^{20})_nS(O)_2 R^{16}$, $-(CR^{19}R^{20})_nS(O)_2NR^{16}R^{17}$, $-(CR^{19}R^{20})_nS(O) (OR^{16})$, $-(CR^{19}R^{20})_nS(O)_2(OR^{16})$, $-(CR^{19}R^{20})_nSC(=Y') R^{16}$, $-(CR^{19}R^{20})_nSC(=Y')OR^{16}$, $-(CR^{19}R^{20})_nSC(=Y') NR^{16}R^{17}$, and $R^{21}$;

each $R^{11'}$ is independently H, $C_1$-$C_{12}$ alkyl, $C_2$-$C_8$ alkenyl, $C_2$-$C_8$ alkynyl, carbocyclyl, heterocyclyl, aryl, or heteroaryl;

$R^{11}$, $R^{12}$ and $R^{13}$ are independently H, $C_1$-$C_{12}$ alkyl, $C_2$-$C_8$ alkenyl, $C_2$-$C_8$ alkynyl, carbocyclyl, heterocyclyl, aryl, or heteroaryl, or $R^{11}$ and $R^{12}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, $CF_3$, $-OCF_3$, $-NO_2$, $C_1$-$C_6$ alkyl, $-OH$, $-SH$, $-O(C_1$-$C_6$ alkyl), $-S(C_1$-$C_6$ alkyl), $-NH_2$, $-NH(C_1$-$C_6$ alkyl), $-N(C_1$-$C_6$ alkyl)$_2$, $-SO_2(C_1$-$C_6$ alkyl), $-CO_2H$, $-CO_2(C_1$-$C_6$ alkyl), $-C(O)NH_2$, $-C(O)NH(C_1$-$C_6$ alkyl), $-C(O)N(C_1$-$C_6$ alkyl)$_2$, $-N(C_1$-$C_6$ alkyl)C(O)($C_1$-$C_6$ alkyl), $-NHC(O)(C_1$-$C_6$ alkyl), $-NHSO_2(C_1$-$C_6$ alkyl), $-N(C_1$-$C_6$ alkyl)SO_2(C_1$-$C_6$ alkyl), $-SO_2NH_2$, $-SO_2NH(C_1$-$C_6$ alkyl), $-SO_2N(C_1$-$C_6$ alkyl)$_2$, $-OC(O)NH_2$, $-OC(O)NH(C_1$-$C_6$ alkyl), $-OC(O)N(C_1$-$C_6$ alkyl)$_2$, $-OC(O)O(C_1$-$C_6$ alkyl), $-NHC(O)NH(C_1$-$C_6$ alkyl), $-NHC(O)N(C_1$-$C_6$ alkyl)$_2$, $-N(C_1$-$C_6$ alkyl)C(O)NH(C_1$-$C_6$ alkyl), $-N(C_1$-$C_6$ alkyl)C(O)N(C_1$-$C_6$ alkyl)$_2$, $-NHC(O)NH(C_1$-$C_6$ alkyl)$_2$, $-NHC(O)N(C_1$-$C_6$ alkyl)$_2$, $-NHC(O)O(C_1$-$C_6$ alkyl), and $-N(C_1$-$C_6$ alkyl)C(O)O(C_1$-$C_6$ alkyl);

$R^{14}$ and $R^{15}$ are independently selected from H, $C_1$-$C_{12}$ alkyl, aryl, carbocyclyl, heterocyclyl, and heteroaryl;

W' is

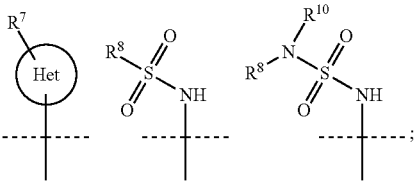

wherein

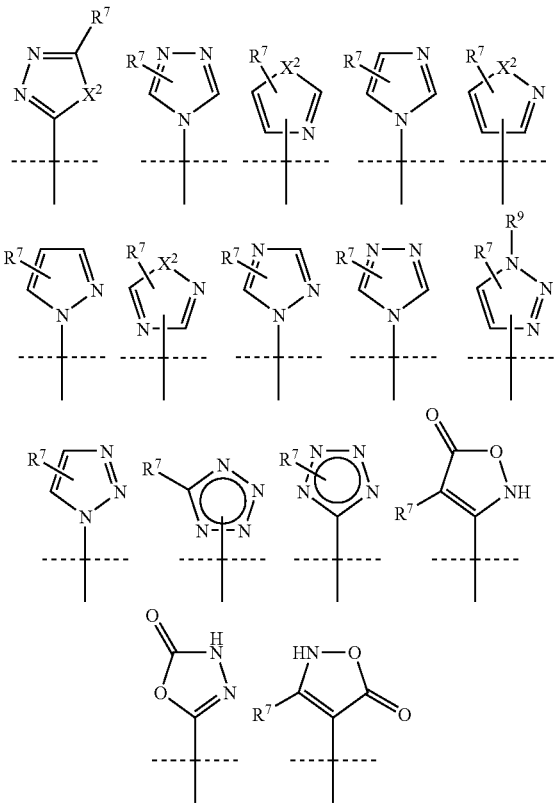

is each $X^2$ is independently O, S, or $NR^9$;

each $R^7$ is independently selected from H, halo, CN, $CF_3$, $-OCF_3$, $-NO_2$, $-(CR^{14}R^{15})_nC(=Y')R^{11}$, $-(CR^{14}R^{15})_nC(=Y')OR^{11}$, $-(CR^{14}R^{15})_nC(=Y')NR^{11}R^{12}$, $-(CR^{14}R^{15})_n NR^{11}R^{12}$, $-(CR^{14}R^{15})_nOR^{11}$, $-(CR^{14}R^{15})_nSR^{11}$, $-(CR^{14}R^{15})_nNR^{12}C(=Y')R^{11}$, $-(CR^{14}R^{15})_nNR^{12}C(=Y') OR^{11}$, $-(CR^{14}R^{15})_nNR^{13}C(=Y')NR^{11}R^{12}$, $-(CR^{14}R^{15})_n NR^{12}SO_2R^{11}$, $-(CR^{14}R^{15})_nOC(=Y')R^{11}$, $-(CR^{14}R^{15})_n OC(=Y')OR^{11}$, $-(CR^{14}R^{15})_nOC(=Y')NR^{11}R^{12}$, $-(CR^{14}R^{15})_nOS(O)_2(OR^{11})$, $-(CR^{14}R^{15})_nOP(=Y') (OR^{11})(OR^{12})$, $-(CR^{14}R^{15})_nOP(OR^{11})(OR^{12})$, $-(CR^{14}R^{15})_nS(O)R^{11}$, $-(CR^{14}R^{15})_nS(O)_2R^{11}$, —(CR$^{14}$R$^{15}$)$_n$S(O)$_2$NR$^{11}$R$^{12}$, —(CR$^{14}$R$^{15}$)$_n$S(O)(OR$^{11}$), —(CR$^{14}$R$^{15}$)$_n$S(O)$_2$(OR$^{11}$), —(CR$^{14}$R$^{15}$)$_n$SC(=Y')R$^{11}$, —(CR$^{14}$R$^{15}$)$_n$SC(=Y')OR$^{11}$, —(CR$^{14}$R$^{15}$)$_n$SC(=Y')NR$^{11}$R$^{12}$, C$_1$-C$_{12}$ alkyl, C$_2$-C$_8$ alkenyl, C$_2$-C$_8$ alkynyl, carbocyclyl, heterocyclyl, aryl, and heteroaryl;

each R$^8$ is independently selected from C$_1$-C$_{12}$ alkyl, aryl, carbocyclyl, heterocyclyl, and heteroaryl;

R$^9$ is selected from H, —(CR$^{14}$R$^{15}$)$_n$C(=Y')R$^{11}$, —(CR$^{14}$R$^{15}$)$_n$C(=Y')OR$^{11}$, —(CR$^{14}$R$^{15}$)$_n$C(=Y')NR$^{11}$R$^{12}$, —(CR$^{14}$R$^{15}$)$_q$NR$^{11}$R$^{12}$, —(CR$^{14}$R$^{15}$)$_q$OR$^{11}$, —(CR$^{14}$R$^{15}$)$_q$SR$^{11}$, —(CR$^{14}$R$^{15}$)$_q$NR$^{12}$C(=Y')R$^{11}$, —(CR$^{14}$R$^{15}$)$_q$NR$^{12}$C(=Y')OR$^{11}$, —(CR$^{14}$R$^{15}$)$_q$NR$^{13}$C(=Y')NR$^{11}$R$^{12}$, —(CR$^{14}$R$^{15}$)$_q$NR$^{12}$SO$_2$R$^{11}$, —(CR$^{14}$R$^{15}$)$_q$OC(=Y')R$^{11}$, —(CR$^{14}$R$^{15}$)$_q$OC(=Y')OR$^{11}$, —(CR$^{14}$R$^{15}$)$_q$OC(=Y')NR$^{11}$R$^{12}$, —(CR$^{14}$R$^{15}$)$_q$OS(O)$_2$(OR$^{11}$), —(CR$^{14}$R$^{15}$)$_q$OP(=Y')(OR$^{11}$)(OR$^{12}$), —(CR$^{14}$R$^{15}$)$_q$OP(OR$^{11}$)(OR$^{12}$), —(CR$^{14}$R$^{15}$)$_n$S(O)R$^{11}$, —(CR$^{14}$R$^{15}$)$_n$S(O)$_2$R$^{11}$, —(CR$^{14}$R$^{15}$)$_n$S(O)$_2$NR$^{11}$R$^{12}$, C$_1$-C$_{12}$ alkyl, C$_2$-C$_8$ alkenyl, C$_2$-C$_8$ alkynyl, carbocyclyl, heterocyclyl, aryl, and heteroaryl;

R$^{10}$ is H, C$_1$-C$_6$ alkyl or C$_3$-C$_4$ carbocyclyl;

X$^4$ is

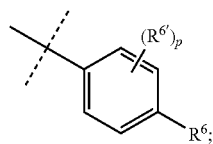

R$^6$ is H, halo, C$_1$-C$_6$ alkyl, C$_2$-C$_8$ alkenyl, C$_2$-C$_8$ alkynyl, carbocyclyl, heteroaryl, heterocyclyl, —OCF$_3$, —NO$_2$, —Si(C$_1$-C$_6$ alkyl), —(CR$^{19}$R$^{20}$)$_n$NR$^{16}$R$^{17}$, —(CR$^{19}$R$^{20}$)$_n$OR$^{16}$, or —(CR$^{19}$R$^{20}$)$_n$—SR$^{16}$;

R$^{6'}$ is H, halo, C$_1$-C$_6$ alkyl, carbocyclyl, CF$_3$, —OCF$_3$, —NO$_2$, —Si(C$_1$-C$_6$ alkyl), —(CR$^{19}$R$^{20}$)$_n$NR$^{16}$R$^{17}$, —(CR$^{19}$R$^{20}$)$_n$OR$^{16}$, —(CR$^{19}$R$^{20}$)$_n$—SR$^{16}$, C$_2$-C$_8$ alkenyl, C$_2$-C$_8$ alkynyl, heterocyclyl, aryl, or heteroaryl;

p is 0, 1, 2 or 3;

n is 0, 1, 2 or 3;

q is 2 or 3;

wherein each said alkyl, alkenyl, alkynyl, carbocyclyl, heterocyclyl, aryl and heteroaryl of R$^1$, R$^2$, R$^3$, R$^4$, R$^5$, R$^6$, R$^{6'}$, R$^7$, R$^8$, R$^9$, R$^{10}$, R$^{11}$, R$^{11'}$, R$^{12}$, R$^{13}$, R$^{14}$, R$^{15}$ and R$^A$ is independently optionally substituted with one or more groups independently selected from halo, CN, CF$_3$, —OCF$_3$, —NO$_2$, oxo, 'Si(C$_1$-C$_6$ alkyl), —(CR$^{19}$R$^{20}$)$_n$C(=Y')R$^{16}$, —(CR$^{19}$R$^2$)$_n$C(=Y')OR$^{16}$, —(CR$^{19}$R$^{20}$)$_n$C(=Y')NR$^{16}$R$^{17}$, —(CR$^{19}$R$^{20}$)$_n$NR$^{16}$R$^{17}$, —(CR$^{19}$R$^{20}$)$_n$OR$^{16}$, —(CR$^{19}$R$^{20}$)$_n$SR$^{16}$, —(CR$^{19}$R$^{20}$)$_n$NR$^{16}$C(=Y')R$^{17}$, —(CR$^{19}$R$^{20}$)$_n$NR$^{16}$C(=Y')OR$^{17}$, —(CR$^{19}$R$^{20}$)$_n$NR$^{18}$C(=Y')NR$^{16}$R$^{17}$, —(CR$^{19}$R$^{20}$)$_n$NR$^{17}$SO$_2$R$^{16}$, —(CR$^{19}$R$^{20}$)$_n$OC(=Y')R$^{16}$, —(CR$^{19}$R$^{20}$)$_n$OC(=Y')OR$^{16}$, —(CR$^{19}$R$^{20}$)$_n$OC(=Y')NR$^{16}$R$^{17}$, —(CR$^{19}$R$^{20}$)$_n$OS(O)$_2$(OR$^{16}$), —(CR$^{19}$R$^{20}$)$_n$OP(=Y')(OR$^{16}$)(OR$^{17}$), —(CR$^{19}$R$^{20}$)$_n$OP(OR$^{16}$)(OR$^{17}$), —(CR$^{19}$R$^{20}$)$_n$S(O)R$^{16}$, —(CR$^{19}$R$^{20}$)$_n$S(O)$_2$R$^{16}$, —(CR$^{19}$R$^{20}$)$_n$S(O)$_2$NR$^{16}$R$^{17}$, —(CR$^{19}$R$^{20}$)$_n$S(O)(OR$^{16}$), —(CR$^{19}$R$^{20}$)$_n$S(O)$_2$(OR$^{16}$), —(CR$^{19}$R$^{20}$)$_n$SC(=Y')R$^{16}$, —(CR$^{19}$R$^{20}$)$_n$SC(=Y')OR$^{16}$, —(CR$^{19}$R$^{20}$)$_n$SC(=Y')NR$^{16}$R$^{17}$, and R$^{21}$;

each R$^{16}$, R$^{17}$ and R$^{18}$ is independently H, C$_1$-C$_{12}$ alkyl, C$_2$-C$_8$ alkenyl, C$_2$-C$_8$ alkynyl, carbocyclyl, heterocyclyl, aryl, or heteroaryl, wherein said alkyl, alkenyl, alkynyl,carbocyclyl, heterocyclyl, aryl, or heteroaryl is optionally substituted with one or more groups selected from halo, CN, —OCF$_3$, CF$_3$, —NO$_2$, C$_1$-C$_6$ alkyl, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

or R$^{16}$ and R$^{17}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, —OCF$_3$, CF$_3$, —NO$_2$, C$_1$-C$_6$ alkyl, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

R$^{19}$ and R$^{20}$ are independently selected from H, C$_1$-C$_{12}$ alkyl, '(CH$_2$)$_n$-aryl, —(CH$_2$)$_n$-carbocyclyl, —(CH$_2$)$_n$-heterocyclyl, and —(CH$_2$)$_n$-heteroaryl;

R$^{21}$ is C$_1$-C$_{12}$ alkyl, C$_2$-C$_8$ alkenyl, C$_2$-C$_8$ alkynyl, carbocyclyl, heterocyclyl, aryl, or heteroaryl, wherein each member of R$^{21}$ is optionally substituted with one or more groups selected from halo, oxo, CN, —OCF$_3$, CF$_3$, —NO$_2$, C$_1$-C$_6$ alkyl, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

each Y' is independently O, NR$^{22}$, or S; and

R$^{22}$ is H or C$_1$-C$_{12}$ alkyl.

The present invention includes a composition (e.g., a pharmaceutical composition) comprising a compound of formula I (and/or solvates, hydrates and/or salts thereof) and a carrier (a pharmaceutically acceptable carrier). The present invention also includes a composition (e.g., a pharmaceutical composition) comprising a compound of formula I (and/or solvates, hydrates and/or salts thereof) and a carrier (a pharmaceutically acceptable carrier), further comprising a second chemotherapeutic and/or a second anti-inflammatory agent. The present compositions are useful for inhibiting abnormal cell growth or treating a hyperproliferative disorder in a mammal (e.g., human). The present compositions are also useful for treating inflammatory diseases in a mammal (e.g., human).

The present invention includes a method of inhibiting abnormal cell growth or treating a hyperproliferative disorder in a mammal (e.g., human) comprising administering to said mammal a therapeutically effective amount of a compound of formula I (and/or solvates and salts thereof) or a composition thereof, alone or in combination with a second chemotherapeutic agent.

The present invention includes a method of treating an inflammatory disease in a mammal (e.g., human) comprising administering to said mammal a therapeutically effective amount of a compound of formula I (and/or solvates and salts thereof) or a composition thereof, alone or in combination with a second anti-inflammatory agent.

The present invention includes a method of using the present compounds for in vitro, in situ, and in vivo diagnosis or treatment of mammalian cells, organisms, or associated pathological conditions.

DETAILED DESCRIPTION OF EXEMPLARY EMBODIMENTS

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Definitions

The term "alkyl" as used herein refers to a saturated linear or branched-chain monovalent hydrocarbon radical of one to twelve carbon atoms. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkenyl" refers to linear or branched-chain monovalent hydrocarbon radical of two to twelve carbon atoms with at least one site of unsaturation, i.e., a carbon-carbon, $sp^2$ double bond, wherein the alkenyl radical includes radicals having "cis" and "trans" orientations, or alternatively, "E" and "Z" orientations. Examples include, but are not limited to, ethylenyl or vinyl (—$CH=CH_2$), allyl (—$CH_2CH=CH_2$), and the like.

The term "alkynyl" refers to a linear or branched monovalent hydrocarbon radical of two to twelve carbon atoms with at least one site of unsaturation, i.e., a carbon-carbon, sp triple bond. Examples include, but are not limited to, ethynyl (—$C\equiv CH$), propynyl (propargyl, —$CH_2C\equiv CH$), and the like.

The terms "carbocycle", "carbocyclyl", "carbocyclic ring" and "cycloalkyl" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronaphthalene, 1,2,3,4-tetrahydronaphthyl, and the like.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "halo" refers to F, Cl, Br or I. The heteroatoms present in heteroaryl or heterocyclyl include the oxidized forms such as $N^+ \rightarrow O^-$, $S(O)$ and $S(O)_2$.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "abnormal cell growth" and "hyperproliferative disorder" are used interchangeably in this application. "Abnormal cell growth", as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small- cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, acute leukemia, as well as head/brain and neck cancer.

A "chemotherapeutic agent" is a compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXO-TERE® (doxetaxel; Rhone-Poulenc Rorer, Antony, France); chloranmbucil; GEMZAR® (gemcitabine); 6-thioguanine; mercaptopurine; methotrexate; platinum analogs such as cis-platin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions (such as any one of the title compounds of EXAMPLES 5-14) are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. No. 5,863,949, U.S. Pat. No. 5,861,510, and EP 780,386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)-quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

Other examples of chemotherapeutic agents that can be used in combination with the present compounds (such as any one of the title compounds of EXAMPLES 5-14) include inhibitors of PI3K (phosphoinositide-3 kinase), such as those reported in Yaguchi et al (2006) Jour. of the Nat. Cancer Inst. 98(8):545-556; U.S. Pat. Nos. 7,173,029; 7,037,915; 6,608,056; 6,608,053; 6,838,457; 6,770,641; 6,653,320; 6,403,588; US 2008/0242665; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070; US 6703414; and WO 97/15658, all of which are incorporated herein in their entireties by reference. Specific examples of such PI3K inhibitors include SF-1126 (PI3K inhibitor, Semafore Pharmaceuticals), BEZ-235 (PI3K inhibitor, Novartis), XL-147 (PI3K inhibitor, Exelixis, Inc.), and GDC-0941 (PI3K inhibitor, Genentech, Inc.).

The term "inflammatory diseases" as used in this application includes, but not limited to, rheumatoid arthritis, atherosclerosis, congestive hear failure, inflammatory bowel disease (including, but not limited to, Crohn's disease and ulcerative colitis), chronic obstructive pulmonary disease in the lung, fibrotic disease in the liver and kidney, Crohn's disease, lupus, skin diseases such as psoriasis, eczema and scleroderma, osteoarthritis, multiple sclerosis, asthma, diseases and disorders related to diabetic complications, fibrotic organ failure in organs such as lung, liver, kidney, and inflammatory complications of the cardiovascular system such as acute coronary syndrome.

An "anti-inflammatory agent" is a compound useful in the treatment of inflammation. Examples of anti-inflammatory agents include injectable protein therapeutics such as Enbrel®, Remicade®, Humira® and Kineret®. Other examples of anti-inflammatory agents include non-steroidal anti-inflammatory agents (NSAIDs), such as ibuprofen or aspirin (which reduce swelling and alleviate pain); disease-modifying anti-rheumatic drugs (DMARDs) such as methotrexate; 5-aminosalicylates (sulfasalazine and the sulfa-free agents); corticosteroids; immunomodulators such as 6-mercaptoputine ("6-MP"), azathioprine ("AZA"), cyclosporines, and biological response modifiers such as Remicade.®. (infliximab) and Enbrel.®. (etanercept); fibroblast growth factors; platelet derived growth factors; enzyme blockers such as Arava.®. (leflunomide); and/or a cartilage protecting agent such as hyaluronic acid, glucosamine, and chondroitin.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof A "liposome" is a small vesicle composed of various types of lipids, phospholipids and/or surfactant which is useful for delivery of a drug (such as the MEK inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis -(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and trialkylsilyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention", "compounds of the present invention" "compounds of formula I", "imidazopyridines" and "imidazopyridines of formula I", unless otherwise indicated, include compounds/imidazopyridines of formula I and stereoisomers, geometric isomers, tautomers, solvates, metabolites, salts (e.g., pharmaceutically acceptable salts) and prodrugs thereof.

The present invention provides imidazopyridines of formula I as described above useful as kinase inhibitors, particularly useful as MEK kinase inhibitors. In an embodiment of the present invention, when $Z^1$ is N, then $R^{11'}$ is not aryl; and all other variables are as defined in formula I.

In an embodiment of the present invention, compounds are of formula I-a and all other variables are as defined in formula I, or as defined in the embodiment described above.

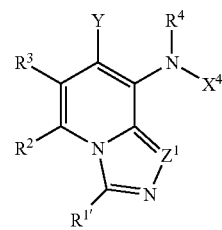

I-a

In an embodiment of the present invention, $R^2$ is H, halo, $CF_3$, or $C_1$-$C_3$ alkyl; and all other variables are as defined in formula I or I-a, or as defined in any one of the embodiments described above.

In another embodiment of the present invention, $R^2$ is H, methyl, $CF_3$, F, or Cl; and all other variables are as defined in formula I or I-a, or as defined in any one of the embodiments described above.

In another embodiment of the present invention, $R^2$ is H, F or Cl; and all other variables are as defined in formula I or I-a, or as defined in any one of the embodiments described above.

In an embodiment of the present invention, $R^3$ is H, halo, $CF_3$, or $C_1$-$C_3$ alkyl; and all other variables are as defined in formula I or I-a, or as defined in any one of the embodiments described above.

In another embodiment of the present invention, $R^3$ is H, methyl, $CF_3$, F, or Cl; and all other variables are as defined in formula I or I-a, or as defined in any one of the embodiments described above.

In another embodiment of the present invention, $R^3$ is H, F or Cl; and all other variables are as defined in formula I or I-a, or as defined in any one of the embodiments described above.

In an embodiment of the present invention, $R^{1'}$ is H or $C_1$-$C_3$ alkyl; and all other variables are as defined in formula I or I-a, or as defined in any one of the embodiments above. In another embodiment, $R^{1'}$ is H, and all other variables are as defined in formula I or I-a, or as defined in any one of the embodiments described above.

In an embodiment of the present invention, $Z^1$ is $CR^1$ and all other variables are as defined in formula I or I-a, or as defined in any one of the embodiments described above.

In an embodiment of the present invention, $Z^1$ is N and all other variables are as defined in formula I or I-a, or as defined in any one of the embodiments described above.

In another embodiment of the present invention, $Z^1$ is $CR^1$ and $R^1$ is H or $C_1$-$C_3$ alkyl; and all other variables are as defined in formula I or I-a, or as defined in any one of the embodiments described above. In another embodiment, $R^1$ is H, and all other variables are as defined in formula I or I-a, or as defined in any one of the embodiments described above. In another embodiment, $R^1$ is methyl, and all other variables are as defined in formula I or I-a, or as defined in any one of the embodiments described above.

In an embodiment of the present invention, $R^4$ is H or $C_1$-$C_6$ alkyl; and all other variables are as defined in formula I or I-a, or as defined in any one of the embodiments above.

In another embodiment of the present invention, $R^4$ is H or methyl; and all other variables are as defined in formula I or I-a, or as defined in any one of the embodiments above. In another embodiment of the present invention, $R^4$ is H; and all other variables are as defined in formula I or I-a, or as defined in any one of the embodiments above.

In an embodiment of the present invention, $R^5$ is H or $C_1$-$C_6$ alkyl; and all other variables are as defined in formula I or I-a, or as defined in any one of the embodiments above.

In another embodiment of the present invention, $R^5$ is H or methyl; and all other variables are as defined in formula I or I-a, or as defined in any one of the embodiments above.

In another embodiment of the present invention, $R^5$ is H; and all other variables are as defined in formula I or I-a, or as defined in any one of the embodiments above.

In another embodiment of the present invention, $R^5$ is methyl; and all other variables are as defined in formula I or I-a, or as defined in any one of the embodiments above.

In an embodiment of the present invention, $X^1$ is $OR^{11'}$; and all other variables are as defined in formula I or I-a; or as defined in any one of the embodiments above.

In another embodiment of the present invention, $X^1$ is $OR^{11'}$ wherein $R^{11'}$ is H or $C_1$-$C_{12}$ alkyl (e.g., $C_1$-$C_6$ alkyl) substituted with one or more groups independently selected from halo, CN, $CF_3$, —$OCF_3$, —$NO_2$, oxo, —$(CR^{19}R^{20})_nC(=Y')R^{16}$, $(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_nSR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$; and all other variables are as defined in formula I or I-a, or as defined in any one of the embodiments above.

In another embodiment of the present invention, $X^1$ is $OR^{11'}$ wherein $R^{11'}$ is heterocyclyl (e.g., 4- to 6-membered heterocyclyl) optionally substituted with one or more groups independently selected from halo, CN, $CF_3$, —$OCF_3$, —$NO_2$, oxo, —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_nSR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$; and all other variables are as defined in formula I or I-a, or as defined in any one of the embodiments above.

In another embodiment of the present invention, $X^1$ is $OR^{11'}$ wherein $R^{11'}$ is 4- to 6-membered heterocyclyl having 1 nitrogen ring atom wherein said heterocyclyl is optionally substituted with one or more groups independently selected from halo, CN, $CF_3$, —$OCF_3$, —$NO_2$, oxo, '$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_nSR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$; and all other variables are as defined in formula I or I-a, or as defined in any one of the embodiments above.

In another embodiment of the present invention, $X^1$ is:

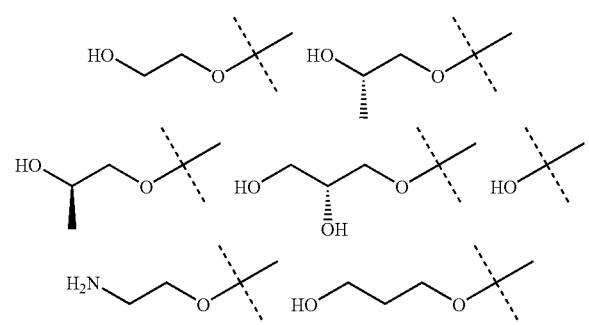

-continued

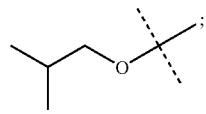

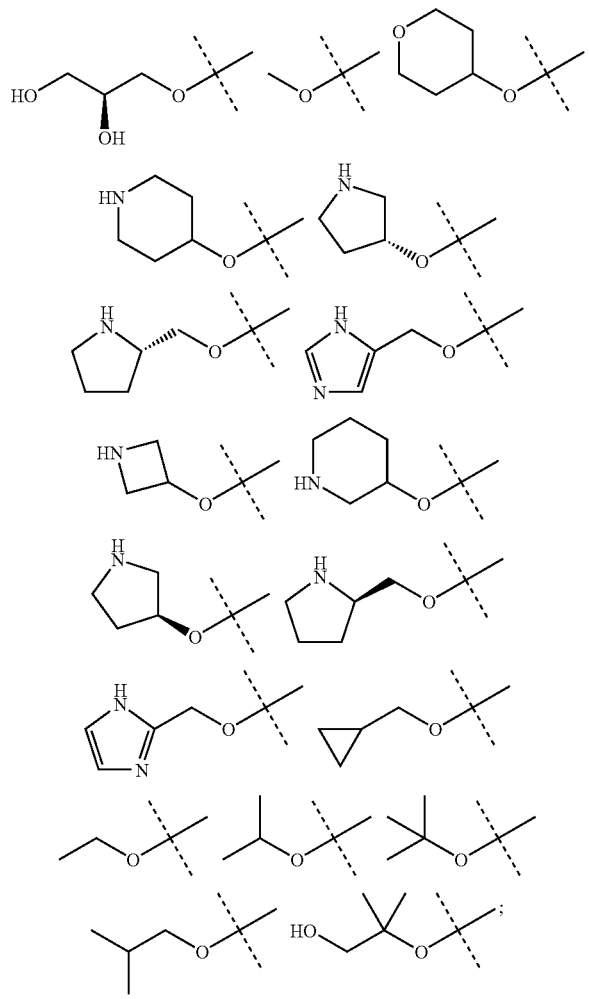

and all other variables are as defined in formula I or I-a, or as defined in any one of the embodiments above.

In another embodiment of the present invention, $X^1$ is

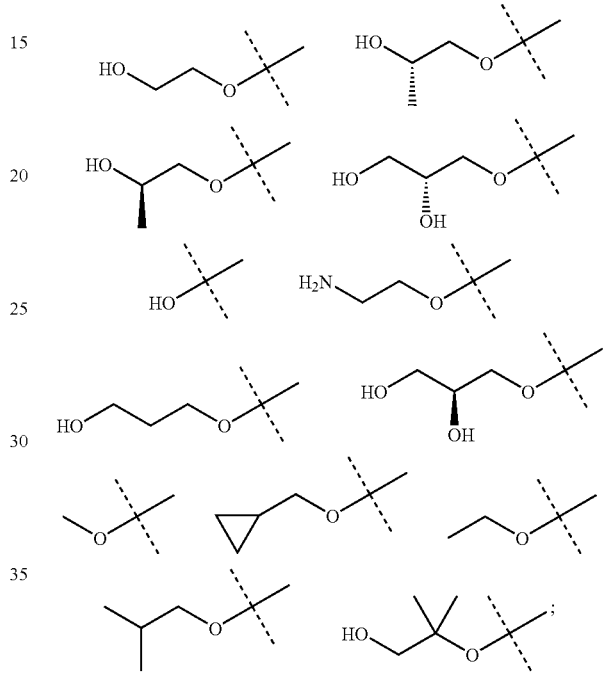

and all other variables are as defined in formula I or I-a, or as defined in any one of the embodiments above.

In an embodiment of the present invention, $X^1$ is $R^{11'}$; and all other variables are as defined in formula I or I-a, or as defined in any one of the embodiments above.

In another embodiment of the present invention, $X^1$ is $R^{11'}$ wherein $R^{11'}$ is H or $C_1$-$C_{12}$ alkyl (e.g., $C_1$-$C_6$ alkyl) substituted with one or more groups independently selected from halo, CN, $CF_3$, —$OCF_3$, —$NO_2$, oxo, —$Si(C_1$-$C_6$ alkyl), —$(CR^{19}R^{20})_n$C(=Y')$R^{16}$, —$(CR^{19}R^{20})_n$C(=Y')$OR^{16}$, —$(CR^{19}R^{20})_n$C(=Y')$NR^{16}R^{17}$, —$(CR^{19}R^{20})_n$NR$^{16}$R$^{17}$, —$(CR^{19}R^{20})_n$OR$^{16}$, —$(CR^{19}R^{20})_n$SR$^{16}$, —$(CR^{19}R^{20})_n$NR$^{16}$C(=Y')$R^{17}$, —$(CR^{19}R^{20})_n$NR$^{16}$C(=Y')$OR^{17}$, —$(CR^{19}R^{20})_n$NR$^{18}$C(=Y')$NR^{16}R^{17}$, —$(CR^{19}R^{20})_n$NR$^{17}$SO$_2$R$^{16}$, —$(CR^{19}R^{20})_n$OC(=Y')$R^{16}$, —$(CR^{19}R^{20})_n$OC(=Y')$OR^{16}$, —$(CR^{19}R^{20})_n$OC(=Y')$NR^{16}R^{17}$, —$(CR^{19}R^{20})_n$OS(O)$_2$(OR$^{16}$), —$(CR^{19}R^{20})_n$OP(=Y')(OR$^{16}$)(OR$^{17}$), —$(CR^{19}R^{20})_n$OP(OR$^{16}$)(OR$^{17}$), —$(CR^{19}R^{20})_n$S(O)R$^{16}$, —$(CR^{19}R^{20})_n$S(O)$_2$R$^{16}$, —$(CR^{19}R^{20})_n$S(O)$_2$NR$^{16}$R$^{17}$, —$(CR^{19}R^{20})_n$S(O)(OR$^{16}$), —$(CR^{19}R^{20})_n$S(O)$_2$(OR$^{16}$), —$(CR^{19}R^2)_n$SC(=Y')$R^{16}$, —$(CR^{19}R^2)_n$SC(=Y')$OR^{16}$, —$(CR^{19}R^{20})_n$SC(=Y')$NR^{16}R^{17}$, and $R^{21}$; and all other variables are as defined in formula I or I-a, or as defined in any one of the embodiments above.

In another embodiment of the present invention, $X^1$ is

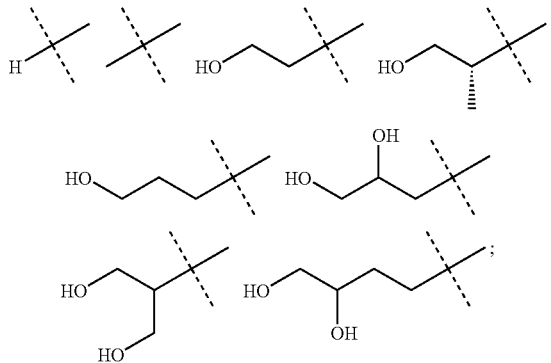

and all other variables are as defined in formula I or I-a, or as defined in any one of the embodiments above.

In another embodiment of the present invention, $R^5$ is H and $X^1$ is

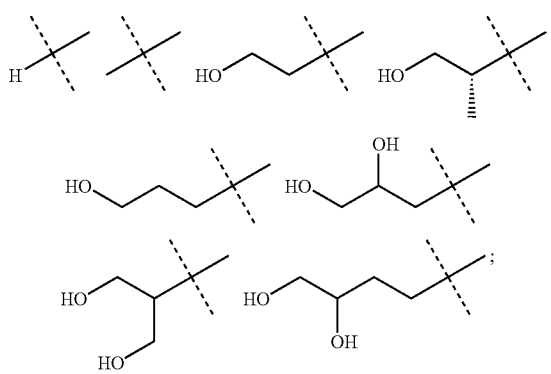

and all other variables are as defined in formula I or I-a, or as defined in any one of the embodiments above.

In another embodiment of the present invention, $X^1$ is

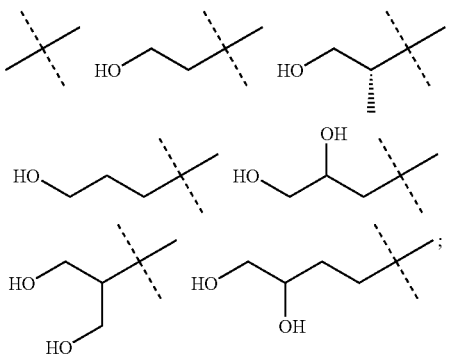

and all other variables are as defined in formula I or I-a, or as defined in any one of the embodiments above.

In another embodiment of the present invention, $R^5$ is methyl and $X^1$ is

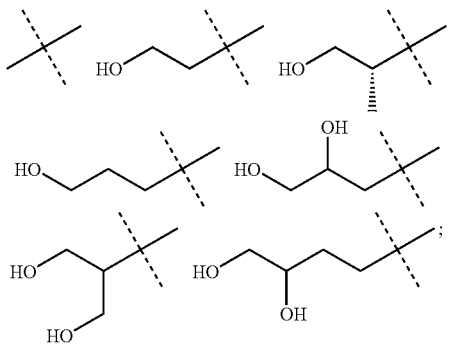

and all other variables are as defined in formula I or I-a, or as defined in any one of the embodiments above.

In an embodiment of the present invention, $X^1$ is $R^{11'}$ and $X^1$ is taken together with $R^5$ and the nitrogen atom to which they are bound to form a 4-5 membered saturated cyclic ring having 0-2 additional heteroatoms selected from O, S and N, wherein said cyclic ring is optionally substituted with one or more groups selected from halo, CN, $CF_3$, $-OCF_3$, $-NO_2$, oxo, $-(CR^{19}R^{20})_nC(=Y')R^{16}$, $-(CR^{19}R^{20})_nC(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_n-SR^{16}$, $-(CR^{19}R^{20})_nNR^{16}C(=Y')R^{17}$, $-(CR^{19}R^{20})_nNR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nOP(=Y')(OR^{16})(OR^{17})$, $-(CR^{19}R^{20})_nOP(OR^{16})(OR^{17})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_nS(O)_2(OR^{16})$, $-(CR^{19}R^{20})_nSC(=Y')R^{16}$, $-(CR^{19}R^{20})_nSC(=Y')OR^{16}$, $-(CR^{19}R^{20})_nSC(=Y')NR^{16}R^{17}$, and $R^{21}$; and all other variables are as defined in formula I or I-a, or as defined in any one of the embodiments above.

In another embodiment of the present invention, W is:

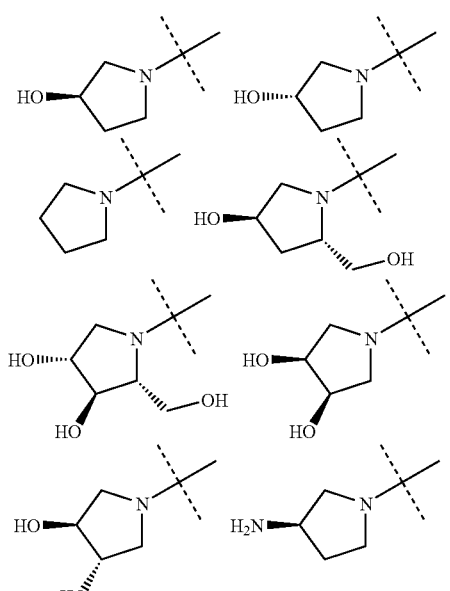

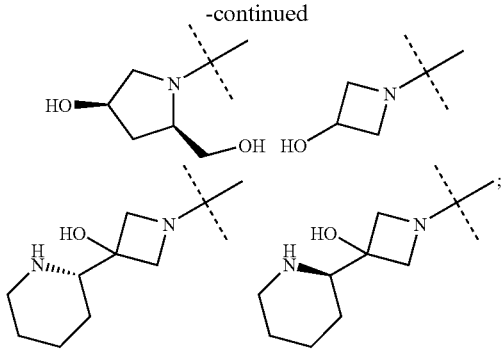

and all other variables are as defined in formula I or I-a, or as defined in any one of the embodiments above.

In an embodiment of the present invention, W is —OR$^{11'}$ wherein R$^{11'}$ is H or $C_1$-$C_{12}$ alkyl; and all other variables are as defined in formula I or I-a, or as defined in any one of the embodiments above.

In another embodiment of the present invention, W is —OR$^{11'}$ wherein R$^{11'}$ is H; and all other variables are as defined in formula I or I-a, or as defined in any one of the embodiments above.

In another embodiment of the present invention, W is —OR$^{11'}$ wherein R$^{11'}$ is $C_1$-$C_6$ alkyl; and all other variables are as defined in formula I or I-a, or as defined in any one of the embodiments above.

In an embodiment of the present invention, W' is —NHSO$_2$R$^8$; and all other variables are as defined in formula I or I-a, or as defined in any one of the embodiments above.

In an embodiment of the present invention, R$^6$ is halo, $C_2$-$C_8$ alkynyl, carbocyclyl, or —SR$^{16}$; and all other variables are as defined in formula I or I-a, or as defined in any one of the embodiments above.

In another embodiment of the present invention, R$^6$ is halo, $C_2$-$C_3$ alkynyl, $C_3$-carbocyclyl, or —SR$^{16}$ wherein R$^{16}$ is $C_1$-$C_2$ alkyl; and all other variables are as defined in formula I or I-a, or as defined in any one of the embodiments above.

In an embodiment of the present invention, R$^{6'}$ is H, halo, or $C_1$-$C_3$ alkyl; and all other variables are as defined in formula I or I-a, or as defined in any one of the embodiments above.

In an embodiment of the present invention, p is 1 or 2; and all other variables are as defined in formula I or I-a, or as defined in any one of the embodiments above.

In an embodiment of the present invention, X$^4$ is

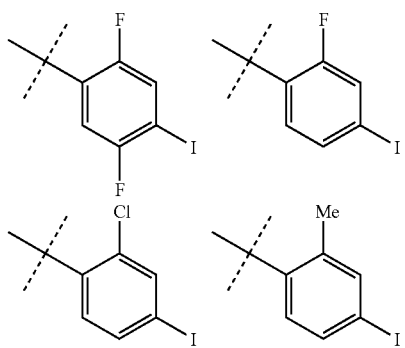

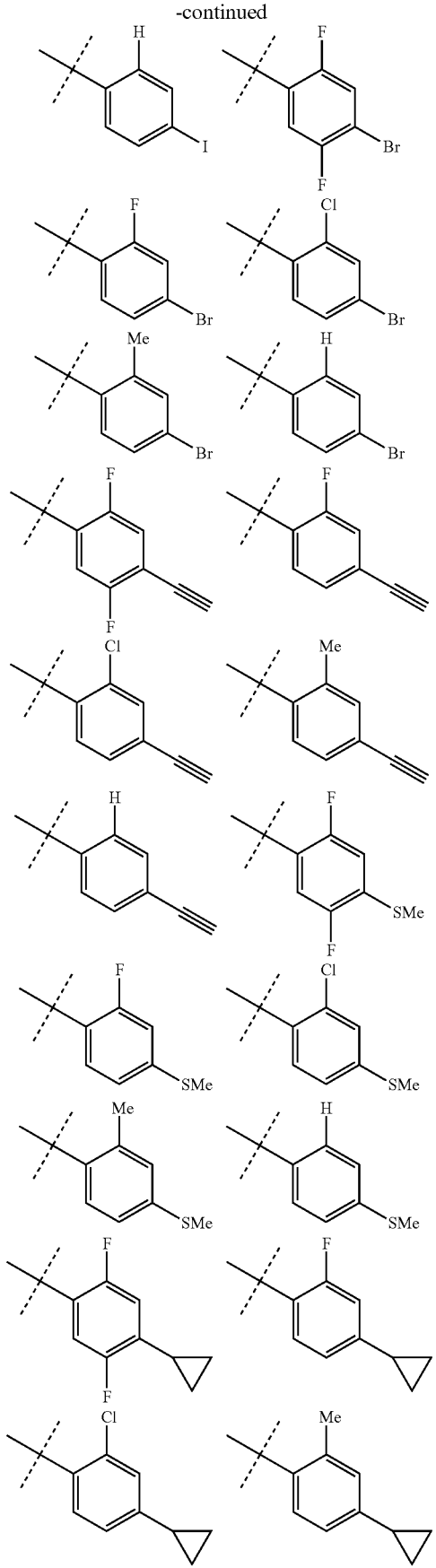

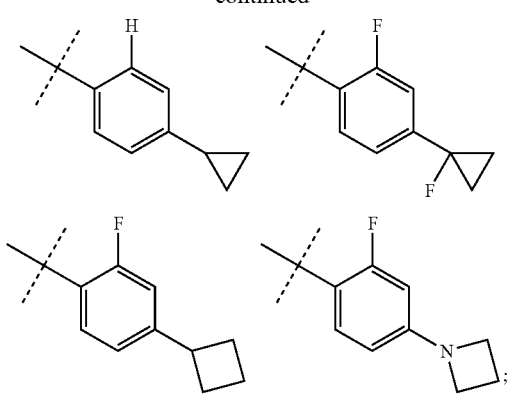

and all other variables are as defined in formula I or I-a, or as defined in any one of the embodiments above.

In another embodiment of the present invention, $X^4$ is

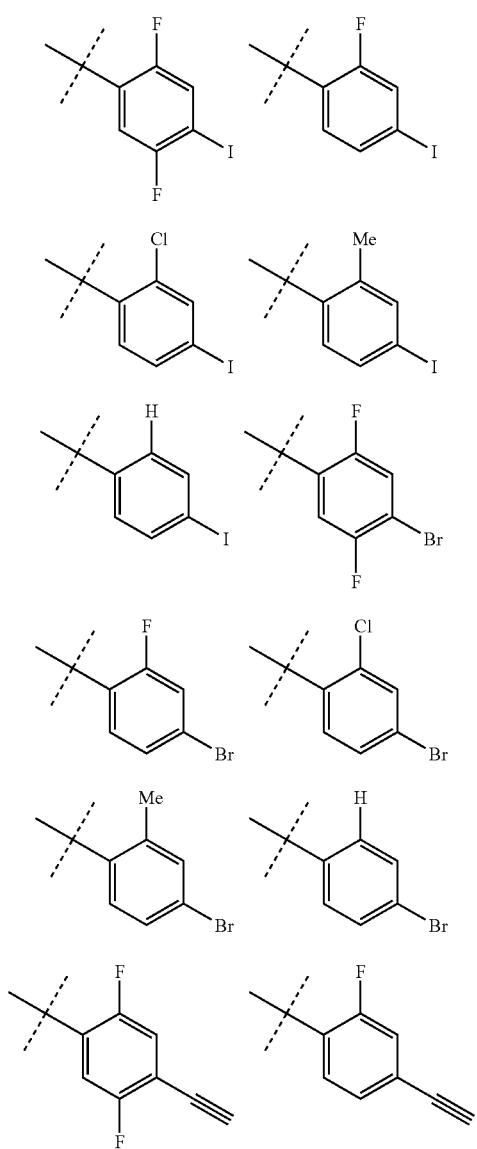

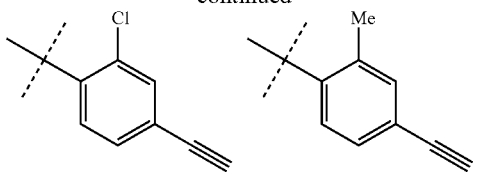

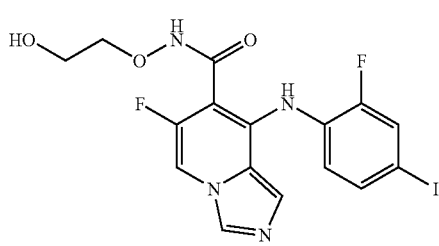

and all other variables are as defined in formula I or I-a, or as defined in any one of the embodiments above.

Another embodiment of the present invention includes compounds described in EXAMPLES 5-14 and compounds below:

-continued
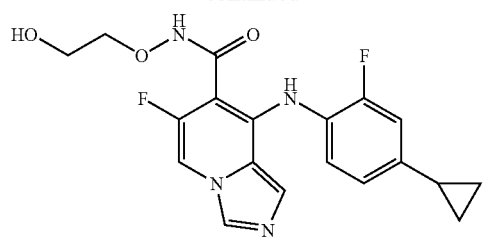
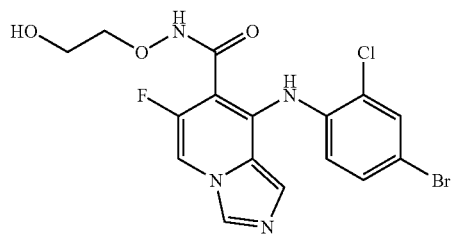
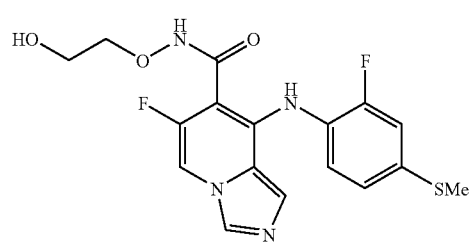
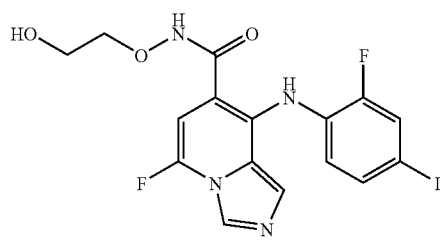
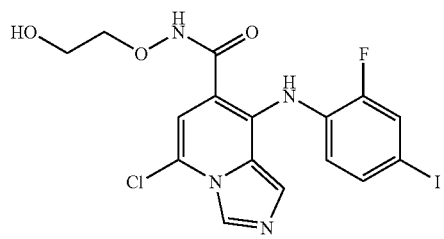
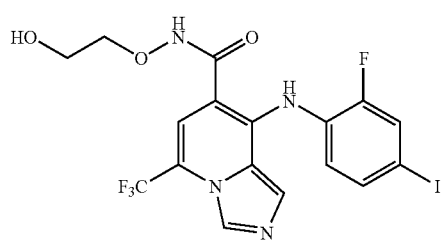
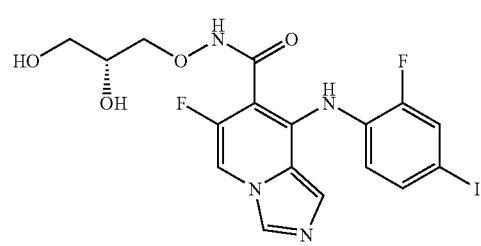
-continued
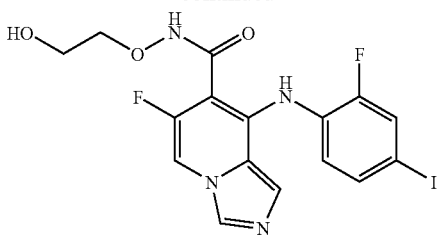
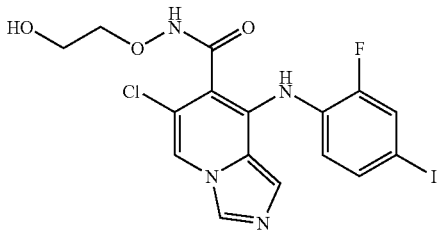
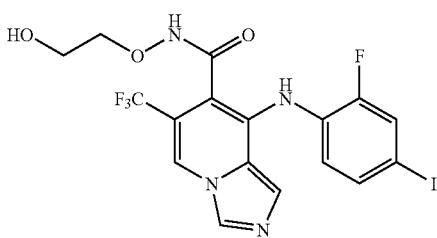
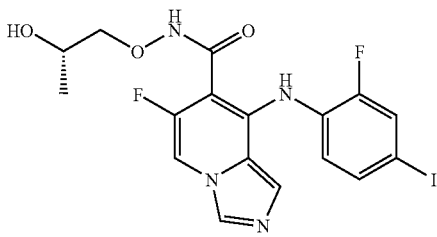
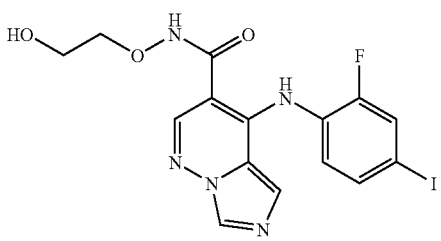
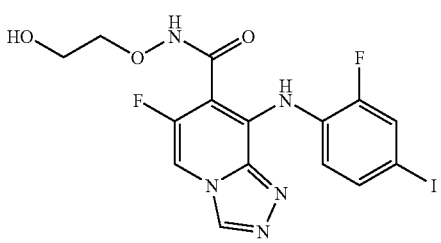
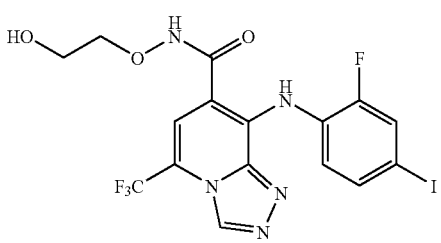

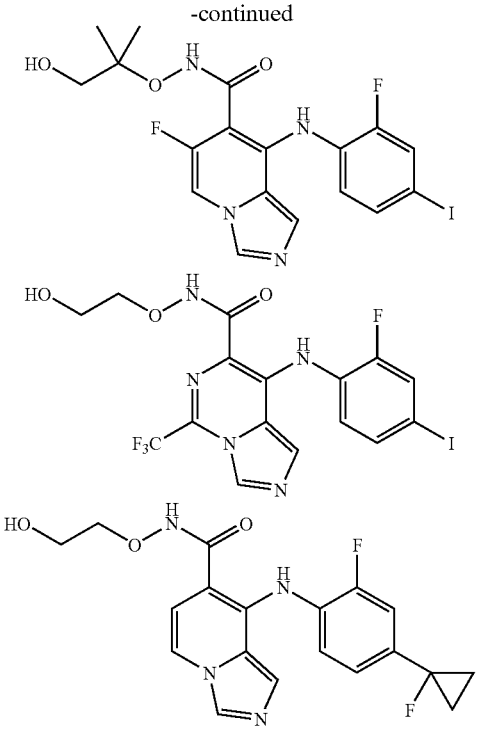
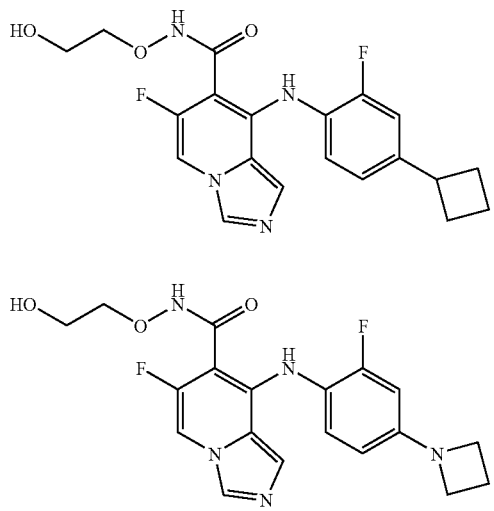
Preparation of Compounds of Formula I
The imidazopyridines of formula I are prepared according to the procedures described below in the schemes and examples or by methods known in the art. For example, compounds of formula (I) where Y=W—C(O)— may be prepared according to Scheme 1.

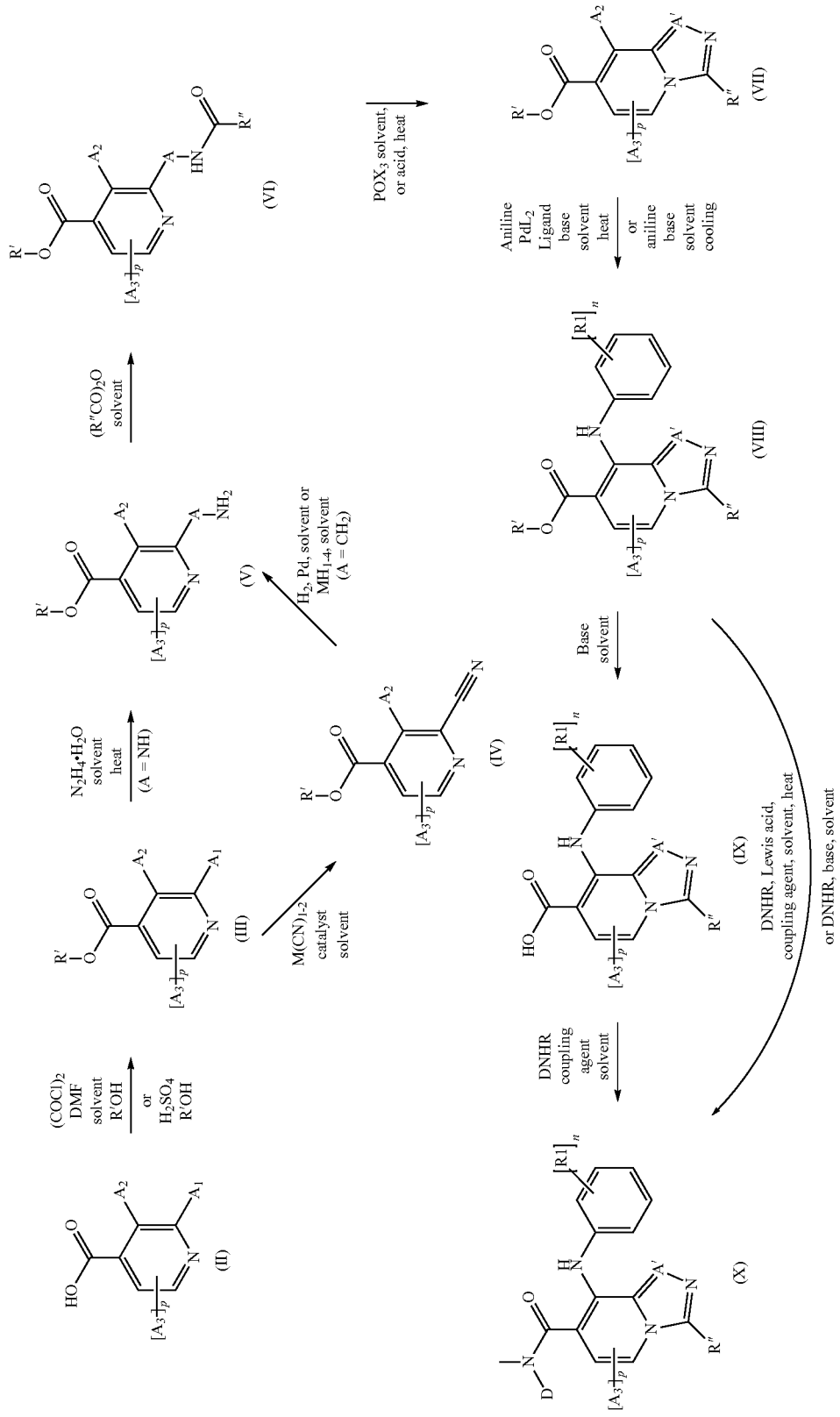

Isonicotinic acids of general structure (II) may be obtained commercially or prepared using methods described in the literature. The acids (II) may be converted in to esters of formula (III) by reaction with a chlorinating agent such as oxalyl chloride, in a presence of a catalyst such as DMF, in a solvent such as DCM, followed by treatment with an alkyl alcohol such methanol. Alternatively acids (II) may be reacted in an alkyl alcohol in the presence of an acid such as sulfuric acid to provide esters of formula (III).

2-Cyanopyridines (IV) may be prepared from 2-halo pyridines (III) by reaction with an inorganic cyanide such as zinc cyanide in the presence of a transition metal catalyst such as Zn, tetrakis(triphenylphosphine)palladium(0) or tris-(dibenzylideneacetone)dipalladium(0)/1,1'-bis(diphenylphosphino)ferrocene, in a solvent such as DMF, at a temperature of from 50° C. to reflux temperature, or under microwave irradiation at a temperature of from 70° C. to 200° C.

Cyano pyridines (IV) may be reduced to give 2-aminomethyl pyridines (V), A=CH$_2$, by reaction with hydrogen at a pressure of from 1 to 5 atmospheres, in the presence of a catalyst such as palladium on carbon, in a solvent such as methanol, acetic acid or formic acid, with or without added strong acid such as concentrated hydrochloric acid. Alternatively, the cyanopyridines (IV) may be converted to 2-aminomethyl pyridines by reacting with an inorganic metal hydride such as sodium borohydride, in the presence of a metal salt such as cobalt chloride, in a solvent such as methanol, at a temperature of from 0° C. to room temperature. Alternatively compounds of formula (V), A=NH, may be prepared from compounds of formula (III) by reaction with hydrazine hydrate, in the presence of a solvent such as ethanol, at a temperature of from 0° C. to reflux.

Compounds of formula (VI) may be prepared from compounds (V) by reaction with an anhydride such as acetic anhydride, or mixed anhydride such as formic-acetic anhydride, in a solvent such as tetrahydrofuran, at a temperature of from 0° C. to reflux.

Compounds of formula (VII) may be prepared from compounds (VI) by reaction with a chlorinating agent such as phosphorous oxychloride, in a solvent such as toluene, at a temperature of from 25° C. to reflux. Alternatively, compounds of formula (VII) may be prepared from compounds of formula (VI) by reaction with an acid such as formic acid, neat or in a solvent such as dioxane, at a temperature of from 50° C. to reflux.

Compounds of formula (VIII) may be prepared from compounds of formula (VII) by reaction with an aniline (incorporating appropriate substituents R1), in the presence of a base such as lithium bis(trimethylsilyl)amide, in a solvent such as THF, at a temperature of from −78° C. to room temperature. Alternatively, compounds of formula (VIII) may be prepared from compounds of formula (VII) by reaction with an aniline (incorporating appropriate substituents R1), in the presence of a catalyst such as tris(dibenzylideneacetone)dipalladium (0), a base such as potassium phosphate, a ligand such as 2-dicyclohexylphosphino-2',6'-(diisopropoxy)biphenyl, in a suitable solvent such as toluene, at a temperature of from room temperature to the reflux temperature of the solvent, or under microwave irradiation at a temperature of from 70° C. to 150° C.

Compounds of formula (IX) can be obtained from compounds of formula (VIII) by reaction with a base such as sodium hydroxide, in a protic solvent such as ethanol or methanol, at a temperature of from room temperature up to reflux temperature.

Compounds of formula (IX) can be reacted with a functionalised hydroxylamine of formula (XII) (commercially available or prepared according to) or an amine, and a suitable coupling agent, such as O-(7-aza-benzo-triazol-1-yl)-N,N,N',N'-tetra-methyluronium hexafluoro-phosphate, N-(3-dimethylaminopropyl)-N'-ethylcarbodiimide hydrochloride or N,N'-dicyclohexylcarbodiimide in the presence of N-hydroxy-1,2,3-benzotriazole, in the presence of a suitable base such as diisopropylethylamine or triethylamine in an inert solvent, such as tetrahydrofuran, N,N-dimethylformamide, or dichloromethane at a temperature of about room temperature, to obtain the compounds of formula (X). Compounds of formula (X) can be obtained directly from compounds of formula (VIII) by reaction with an amine or hydroxylamine DNHR in the presence of a Lewis acid such as trimethyl aluminium in a solvent such as DCM, at a temperature of from room temperature up to reflux temperature. Alternatively, compounds of formula (X) may be prepared from compounds of formula (VIII) by treatment with a functionalized hydroxylamine DNHR in the presence of a base such as lithium bis(trimethylsilyl)amide in a solvent such as THF at a temperature of from −78° C. to 25° C.

Compounds of formula (I) where Y=R$^8$SO$_2$NH— May be prepared according to Scheme 2.

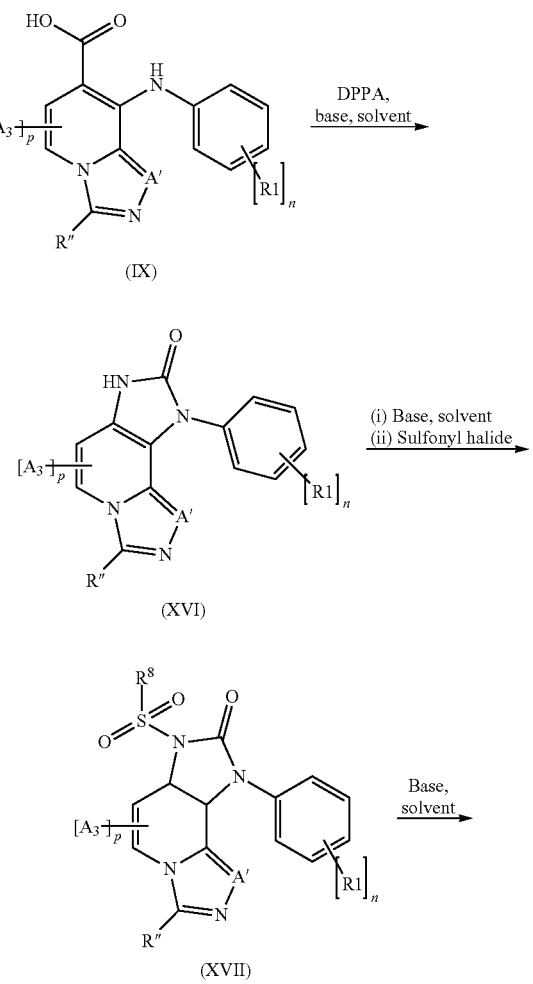

-continued

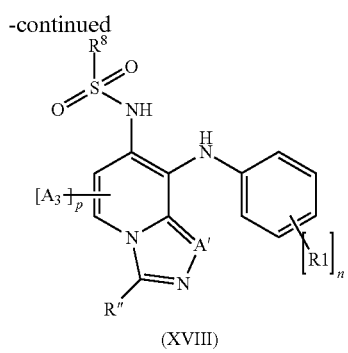

(XVIII)

Compounds of formula (XVI) may be prepared from compounds of formula (IX) by treatment with diphenylphosphoryl azide in a solvent such as toluene, in the presence of a base such as triethylamine. Compounds of formula (XVII) may be prepared from compounds of formula (XVI) by treatment with a base such as sodium hydride, in a solvent such as DMF, followed by reaction with a sulfonyl chloride (appropriately substituted). Compounds of formula (XVIII) may be prepared from compounds of formula (XVII) by deprotection using a base such as sodium hydroxide in a solvent such as DMF at a temperature of from 50° C. to 150° C.

Hydroxylamines of formula (XII) may be prepared using methods described in the literature or the synthetic route outlined in Scheme 3.

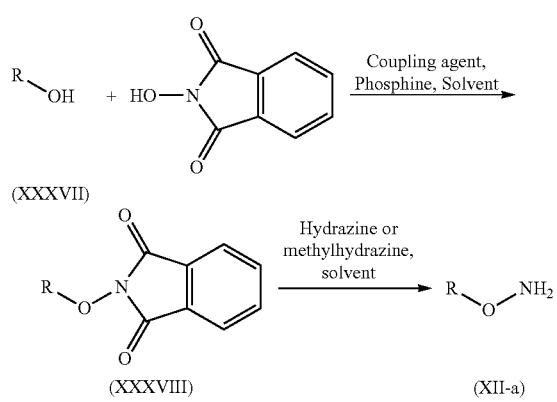

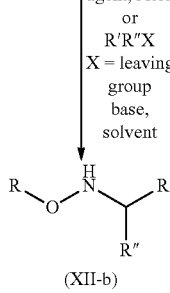

(XII-b)

Primary or secondary alcohols of general formula (XXXVII) may be prepared using methods described in the literature. They may be reacted with N-hydroxy phthalimide using a phosphine and coupling reagent such as diethyl azodicarboxylate to provide compounds of general formula (XXXVIII). Compounds of general formula (XXXVIII) may be deprotected using hydrazine or methyl hydrazine to provide hydroxylamines of general formula (XII-a).

Compounds of formula (XII-a) may be further modified by reductive amination with aldehydes or ketones using a reducing agent such as sodium triacetoxy borohydride, sodium cyanoborohydride, or borane-pyridine in a solvent such as dichloroethane at a temperature of from ambient temperature to reflux. In addition, compounds of formula (XII-a) may be further modified by alkylation with an alkyl halide in the presence of a base such as triethylamine, in a solvent such as dichloromethane, to provide hydroxylamines of general formula (XII-b).

Alternatively, hydroxylamines of formula (XII-a) may be prepared according to Scheme 4.

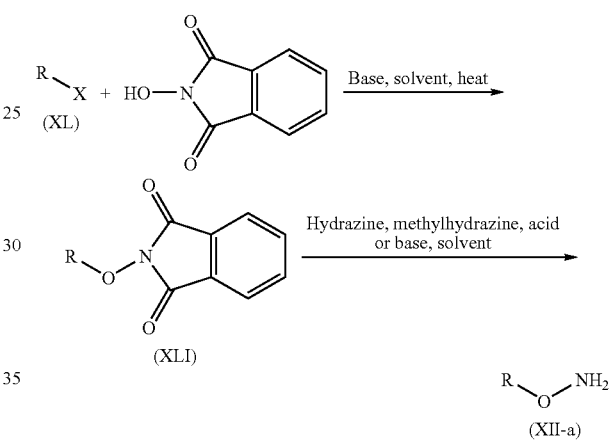

Alkyl halides of formula (XL) may be reacted with N-hydroxy phthalimide in the presence of a base such as potassium carbonate in a solvent such as dimethyl sulfoxide at a temperature of from 10° C. to 50° C. Compounds of formula (XLI) may be converted to compounds of formula (XII) using the methods described for the conversion of compounds of formula (XXXVIII) to compounds of formula (XII) in Scheme 3.

Alternatively, compounds of formula (XII-a) may be prepared according to Scheme 5.

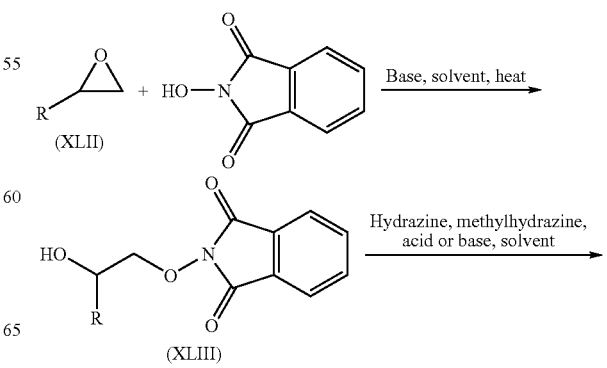

-continued

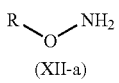

(XII-a)

Compounds of formula (XLII) may be reacted with N-hydroxy phthalimide in the presence of a catalytic amount of a base such as DIPEA and a co-catalyst such as tetra-butyl ammonium bromide in a solvent such as toluene at a temperature of form 50° C. to reflux. Compounds of formula (XLIII) may be converted to compounds of formula (XII) using the methods described for the conversion of compounds of formula (XXXVIII) to compounds of formula (XII) in Scheme 3.

Anilines of general formula (XXXI) used in cross-coupling reactions described above may be prepared by using methods described in the literature or according to Scheme 6.

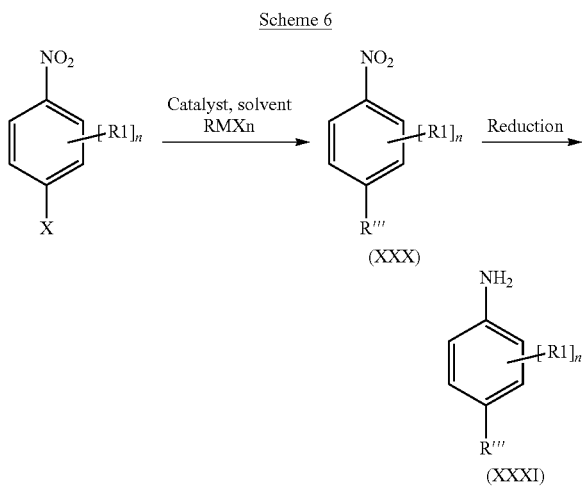

Where $R_1$ is an optional substituent group, n = 0-4
R''' = alkyl, cycloalkyl, vinyl, SiMe$_3$ Substituted 1-chloro-4-nitro benzene may be reacted with a metal RMXn such as cyclopropyl boronic acid or hexamethyldisilazane, in a solvent such as xylene, using a catalyst such as tetrakis(triphenylphosphine)palladium, at a temperature of from room temperature to reflux to give compounds of formula (XXX). The nitro group may be reduced using methods described in the literature such as reaction under an atmosphere of hydrogen at a pressure of from 1 to 5 atmospheres, in the presence of a catalyst such as palladium on carbon, and in a solvent such as ethanol or ethyl acetate at room temperature, to give compounds of formula (XXXI).

Alternatively, anilines of formula (LV) may be prepared according to Scheme 7.

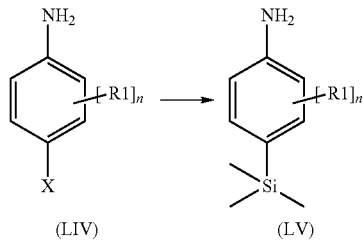

X = Br, I

4-Bromo or iodo anilines of formula (LIV) may be reacted with at least 2 equivalents of a strong organometallic base such as n-butyllithium in a solvent such as THF at a temperature of from −100° C. to −20° C. followed by quench of the intermediate aryl lithium species with an electrophile such as trimethyl silyl chloride to give compounds of formula (LV).

It will be appreciated that where appropriate functional groups exist, compounds of formula (I) or any intermediates used in their preparation may be further derivatised by one or more standard synthetic methods employing substitution, oxidation, reduction, or cleavage reactions. Particular substitution approaches include conventional alkylation, arylation, heteroarylation, acylation, sulfonylation, halogenation, nitration, formylation and coupling procedures.

For example, aryl bromide or chloride groups may be converted to aryl iodides using a Finkelstein reaction employing an iodide source such as sodium iodide, a catalyst such as copper iodide and a ligand such as trans-N,N'-dimethyl-1,2-cyclohexane diamine in a solvent such as 1,4-dioxane and heating the reaction mixture at reflux temperature. Aryl trialkylsilanes may be converted to aryl iodides by treating the silane with an iodide source such as iodine monochloride in a solvent such as dichloromethane with or without Lewis acid such as silver tetrafluoroborate at a temperature from −40° C. to reflux.

In a further example primary amine (—NH$_2$) groups may be alkylated using a reductive alkylation process employing an aldehyde or a ketone and a borohydride, for example sodium triacetoxyborohydride or sodium cyanoborohydride, in a solvent such as a halogenated hydrocarbon, for example 1,2-dichloroethane, or an alcohol such as ethanol, where necessary in the presence of an acid such as acetic acid at around ambient temperature. Secondary amine (—NH—) groups may be similarly alkylated employing an aldehyde.

In a further example, primary amine or secondary amine groups may be converted into amide groups (—NHCOR' or —NRCOR') by acylation. Acylation may be achieved by reaction with an appropriate acid chloride in the presence of a base, such as triethylamine, in a suitable solvent, such as dichloromethane, or by reaction with an appropriate carboxylic acid in the presence of a suitable coupling agent such HATU (O-(7-azabenzotriazol-1-yl)-N,N,N',N'-tetramethyluronium hexafluorophosphate) in a suitable solvent such as dichloromethane. Similarly, amine groups may be converted into sulfonamide groups (—NHSO$_2$R' or —NR"SO$_2$R') by reaction with an appropriate sulfonyl chloride in the presence of a suitable base, such as triethylamine, in a suitable solvent such as dichloromethane. Primary or secondary amine groups can be converted into urea groups (—NHCONR'R" or —NRCONR'R") by reaction with an appropriate isocyanate in the presence of a suitable base such as triethylamine, in a suitable solvent, such as dichloromethane.

An amine (—NH$_2$) may be obtained by reduction of a nitro (—NO$_2$) group, for example by catalytic hydrogenation, using for example hydrogen in the presence of a metal catalyst, for example palladium on a support such as carbon in a solvent such as ethyl acetate or an alcohol e.g. methanol. Alternatively, the transformation may be carried out by chemical reduction using for example a metal, e.g. tin or iron, in the presence of an acid such as hydrochloric acid.

In a further example, amine (—CH$_2$NH$_2$) groups may be obtained by reduction of nitriles (—CN), for example by catalytic hydrogenation using for example hydrogen in the presence of a metal catalyst, for example palladium on a support such as carbon, or Raney nickel, in a solvent such as an ether e.g. a cyclic ether such as tetrahydrofuran, at a temperature from −78° C. to the reflux temperature of the solvent.

In a further example, amine (—NH$_2$) groups may be obtained from carboxylic acid groups (—CO$_2$H) by conversion to the corresponding acyl azide (—CON$_3$), Curtius rearrangement and hydrolysis of the resultant isocyanate (—N=C=O).

Aldehyde groups (—CHO) may be converted to amine groups (—CH$_2$NR'R")) by reductive amination employing an amine and a borohydride, for example sodium triacetoxyborohydride or sodium cyanoborohydride, in a solvent such as a halogenated hydrocarbon, for example dichloromethane, or an alcohol such as ethanol, where necessary in the presence of an acid such as acetic acid at around ambient temperature.

In a further example, aldehyde groups may be converted into alkenyl groups (—CH=CHR') by the use of a Wittig or Wadsworth-Emmons reaction using an appropriate phosphorane or phosphonate under standard conditions known to those skilled in the art.

Aldehyde groups may be obtained by reduction of ester groups (such as —CO$_2$Et) or nitriles (—CN) using diisobutylaluminium hydride in a suitable solvent such as toluene. Alternatively, aldehyde groups may be obtained by the oxidation of alcohol groups using any suitable oxidising agent known to those skilled in the art.

Ester groups (—CO$_2$R') may be converted into the corresponding acid group (—CO$_2$H) by acid- or base-catalused hydrolysis, depending on the nature of R. If R is t-butyl, acid-catalysed hydrolysis can be achieved for example by treatment with an organic acid such as trifluoroacetic acid in an aqueous solvent, or by treatment with an inorganic acid such as hydrochloric acid in an aqueous solvent.

Carboxylic acid groups (—CO$_2$H) may be converted into amides (CONHR' or —CONR'R") by reaction with an appropriate amine in the presence of a suitable coupling agent, such as HATU, in a suitable solvent such as dichloromethane.

In a further example, carboxylic acids may be homologated by one carbon (i.e —CO$_2$H to —CH$_2$CO$_2$H) by conversion to the corresponding acid chloride (—COCl) followed by Arndt-Eistert synthesis.

In a further example, —OH groups may be generated from the corresponding ester (e.g. —CO$_2$R'), or aldehyde (—CHO) by reduction, using for example a complex metal hydride such as lithium aluminium hydride in diethyl ether or tetrahydrofuran, or sodium borohydride in a solvent such as methanol. Alternatively, an alcohol may be prepared by reduction of the corresponding acid (—CO$_2$H), using for example lithium aluminium hydride in a solvent such as tetrahydrofuran, or by using borane in a solvent such as tetrahydrofuran.

Alcohol groups may be converted into leaving groups, such as halogen atoms or sulfonyloxy groups such as an alkylsulfonyloxy, e.g. trifluoromethylsulfonyloxy or arylsulfonyloxy, e.g. p-toluenesulfonyloxy group using conditions known to those skilled in the art. For example, an alcohol may be reacted with thioyl chloride in a halogenated hydrocarbon (e.g. dichloromethane) to yield the corresponding chloride. A base (e.g. triethylamine) may also be used in the reaction.

In another example, alcohol, phenol or amide groups may be alkylated by coupling a phenol or amide with an alcohol in a solvent such as tetrahydrofuran in the presence of a phosphine, e.g. triphenylphosphine and an activator such as diethyl-, diisopropyl, or dimethylazodicarboxylate. Alternatively alkylation may be achieved by deprotonation using a suitable base e.g. sodium hydride followed by subsequent addition of an alkylating agent, such as an alkyl halide.

Aromatic halogen substituents in the compounds may be subjected to halogen-metal exchange by treatment with a base, for example a lithium base such as n-butyl or t-butyl lithium, optionally at a low temperature, e.g. around −78° C., in a solvent such as tetrahydrofuran, and then quenched with an electrophile to introduce a desired substituent. Thus, for example, a formyl group may be introduced by using N,N-dimethylformamide as the electrophile. Aromatic halogen substituents may alternatively be subjected to metal (e.g. palladium or copper) catalysed reactions, to introduce, for example, acid, ester, cyano, amide, aryl, heteraryl, alkenyl, alkynyl, thio- or amino substituents. Suitable procedures which may be employed include those described by Heck, Suzuki, Stille, Buchwald or Hartwig.

Aromatic halogen substituents may also undergo nucleophilic displacement following reaction with an appropriate nucleophile such as an amine or an alcohol. Advantageously, such a reaction may be carried out at elevated temperature in the presence of microwave irradiation.

The compounds of the present invention are tested for their capacity to inhibit MEK activity and activation (primary assays) and for their biological effects on growing cells (secondary assays) as described below. The compounds of the present invention having IC$_{50}$ of less than 5 µM (more preferably less than 0.1 µM, most preferably less than 0.01 µM) in the MEK activity assay of Example 1, IC$_{50}$ of less than 5 µM (more preferably less than 1 µM, even more preferably less than 0.1 µM, most preferably less than 0.01 µM) in the MEK activation assay of Example 2, EC$_{50}$ of less than 10 µM (more preferably less than 1 µM, even more preferably less than 0.5 µM, most preferably less than 0.1 µM) in the cell proliferation assay of Example 3, and/or EC$_{50}$ of less than 10 µM (more preferably less than 1 µM, even more preferably less than 0.5 µM, most preferably less than 0.1 µM) in the ERK phosphorylation assay of Example 4, are useful as MEK inhibitors.

The present invention includes a composition (e.g., a pharmaceutical composition) comprising a compound of formula I (and/or solvates and/or salts thereof) and a carrier (a pharmaceutically acceptable carrier). The present invention also includes a composition (e.g., a pharmaceutical composition) comprising a compound of formula I (and/or solvates and/or salts thereof) and a carrier (a pharmaceutically acceptable carrier), further comprising a second chemotherapeutic and/or a second anti-inflammatory agent such as those described herein. The present compositions are useful for inhibiting abnormal cell growth or treating a hyperproliferative disorder in a mammal (e.g., human). The present compositions are also useful for treating inflammatory diseases in a mammal (e.g., human).

The present compounds and compositions are also useful for treating an autoimmune disease, destructive bone disorder, proliferative disorders, infectious disease, viral disease, fibrotic disease or neurodegenerative disease in a mammal (e.g., human). Examples of such diseases/disorders include, but are not limited to, diabetes and diabetic complications, diabetic retinopathy, retinopathy of prematurity, age-related macular degeneration, hemangioma, idiopathic pulmonary fibrosis, rhinitis and atopic dermatitis, renal disease and renal failure, polycystic kidney disease, congestive heart failure, neurofibromatosis, organ transplant rejection, cachexia, stroke, septic shock, heart failure, organ transplant rejection, Alzheimer's disease, chronic or neuropathic pain, and viral infections such as HIV, hepatitis (B) virus (HBV), human papilloma virus (HPV), cytomegalovirus (CMV), and Epstein-Barr virus (EBV). Chronic pain, for purposes of the present invention includes, but is not limited to, idiopathic pain, and pain associated with chronic alcoholism, vitamin deficiency, uremia, hypothyroidism, inflammation, arthritis, and post-operative pain. Neuropathic pain is associated with numerous conditions which include, but are not limited to, inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, arthritis pain, and nerve injury between the peripheral nervous system and the central nervous system.

The present compounds and compositions are also useful for treating pancreatitis or kidney disease (including proliferative glomerulonephritis and diabetes-induced renal disease) in a mammal (e.g., human).

The present compounds and compositions are also useful for the prevention of blastocyte implantation in a mammal (e.g., human).

The present invention includes a method of inhibiting abnormal cell growth or treating a hyperproliferative disorder in a mammal (e.g., human) comprising administering to said mammal a therapeutically effective amount of a compound of formula I (and/or solvates and/or salts thereof) or a composition thereof. Also included in the present invention is a method of treating an inflammatory disease in a mammal (e.g., human) comprising administering to said mammal a therapeutically effective amount of a compound of formula I (and/or solvates and/or salts thereof) or a composition thereof.

The present invention includes a method of inhibiting abnormal cell growth or treating a hyperproliferative disorder in a mammal (e.g., human) comprising administering to said mammal a therapeutically effective amount of a compound of formula I (and/or solvates and/or salts thereof) or a composition thereof, in combination with a second chemotherapeutic agent such as those described herein. The present invention also includes a method of treating an inflammatory disease in a mammal (e.g., human) comprising administering to said mammal a therapeutically effective amount of a compound of formula I (and/or solvates and/or salts thereof) or a composition thereof, in combination with a second anti-inflammatory agent such as those described herein.

The present invention includes a method of treating an autoimmune disease, destructive bone disorder, proliferative disorders, infectious disease, viral disease, fibrotic disease or neurodegenerative disease in a mammal (e.g., human) comprising administering to said mammal a therapeutically effective amount of a compound of formula I (and/or solvates and salts thereof) or a composition thereof, and optionally further comprising a second therapeutic agent. Examples of such diseases/disorders include, but are not limited to, diabetes and diabetic complications, diabetic retinopathy, retinopathy of prematurity, age-related macular degeneration, hemangioma, idiopathic pulmonary fibrosis, rhinitis and atopic dermatitis, renal disease and renal failure, polycystic kidney disease, congestive heart failure, neurofibromatosis, organ transplant rejection, cachexia, stroke, septic shock, heart failure, organ transplant rejection, Alzheimer's disease, chronic or neuropathic pain, and viral infections such as HIV, hepatitis (B) virus (HBV), human papilloma virus (HPV), cytomegalovirus (CMV), and Epstein-Barr virus (EBV).

The present invention includes a method of treating pancreatitis or kidney disease (including proliferative glomerulonephritis and diabetes-induced renal disease) in a mammal (e.g., human) comprising administering to said mammal a therapeutically effective amount of a compound of formula I (and/or solvates and salts thereof) or a composition thereof, and optionally further comprising a second therapeutic agent.

The present invention includes a method for preventing of blastocyte implantation in a mammal (e.g., human) comprising administering to said mammal a therapeutically effective amount of a compound of formula I (and/or solvates and salts thereof) or a composition thereof, and optionally further comprising a second therapeutic agent.

The present invention includes a method of using the present compounds for in vitro, in situ, and in vivo diagnosis or treatment of mammalian cells, organisms, or associated pathological conditions.

It is also believed that the compounds of the present invention can render abnormal cells more sensitive to treatment with radiation for purposes of killing and/or inhibiting the growth of such cells. Accordingly, this invention further relates to a method for sensitizing abnormal cells in a mammal (e.g., human) to treatment with radiation which comprises administering to said mammal an amount of a compound of formula I (and/or solvates and salts thereof) or a composition thereof, which amount is effective is sensitizing abnormal cells to treatment with radiation.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, inhalation and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or in combination with one or more chemotherapeutic or anti-inflammatory agents, for example those described herein. Such conjoint treatment may be achieved by way of the simultaneous, sequential or separate dosing of the individual components of treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof Methods of preparing various pharmaceutical compositions with a specific amount of active compound are known, or will be apparent, to those skilled in this art. For examples, see Remington's Pharmaceutical Sciences, Mack Publishing Company, Ester, Pa., 15.sup.th Edition (1975).

EXAMPLES

| Abbreviations | |
|---|---|
| nBuLi | n-Butyllithium |
| $CDCl_3$ | Deuterated chloroform |
| $CD_3OD$ | Deuterated methanol |
| DCM | Dichloromethane |
| DIPEA | Diisopropylethylamine |
| DMF | Dimethylformamide |
| DMSO | Dimethylsulfoxide |
| Dppf | 1,1'-Bis(diphenylphosphino)ferrocene |
| EDCI | 1-Ethyl-3-(3'-dimethylaminopropyl)carbodiimide hydrochloride |
| $Et_3N$ | Triethylamine |
| HATU | O-(7-Azabenzotriazol-1-yl)-N,N,N',N'-tetramethyluronium hexafluorophosphate |
| HCl | Hydrochloric acid |
| Hyflo ® | Diatomaceous earth |
| HOBt | 1-Hydroxybenzotriazole |
| IMS | Industrial methylated spirits |
| $K_3PO_4$ | Potassium phosphate tribasic |
| LHMDS | Lithium bis(trimethylsilyl)amide |
| MeOH | Methanol |
| NaOH | Sodium hydroxide |
| $Pd(PPh_3)_4$ | Tetrakis(triphenylphosphine)palladium(0) |
| $Pd_2dba_3$ | Tris-(dibenzylideneacetone)dipalladium(0) |
| Si-PPC | Pre-packed silica flash chromatography cartridge: Isolute ® SPE, Biotage SNAP ® or ISCO Redisep ® |
| SCX-2 | Isolute ® silica-based sorbent with a chemically bonded propylsulfonic acid functional group. |
| THF | Tetrahydrofuran |

General Experimental Conditions $^1$H NMR spectra were recorded at ambient temperature using a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography-Mass Spectrometry (LCMS) experiments to determine retention times ($R_T$) and associated mass ions were performed using one of the following methods.

Method A: Experiments performed on a Waters Micromass ZQ quadrupole mass spectrometer linked to a Hewlett Packard HP 1100 LC system with diode array detector. This system uses a Higgins Clipeus 5 micron C18 100×3.0 mm column and a 1 ml/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 5 minutes.

Method B: Experiments performed on a Waters Platform LC quadrupole mass spectrometer linked to a Hewlett Packard HP1100 LC system with diode array detector and 100 position autosampler using a Phenomenex Luna C18(2) 30×4.6 mm column and a 2 ml/minute flow rate. The solvent system was 95% water containing 0.1% formic acid (solvent A) and 5% acetonitrile containing 0.1% formic acid (solvent B) for the first 0.50 minutes followed by a gradient up to 5% solvent A and 95% solvent B over the next 4 minutes. The final solvent system was held constant for a further 0.50 minutes.

Microwave experiments were carried out using a Personal Chemistry Emrys Iniatiator™ or Optimizer™, which uses a single-mode resonator and dynamic field tuning, both of which give reproducibility and control. Temperature from 40-250° C. can be achieved, and pressures of up to 20bar can be reached.

Example 1

MEK Assay (MEK Activity Assay)

Constitutively activated human mutant MEK1 expressed in insect cells is used as source of enzymatic activity at a final concentration in the kinase assay of 15 nM.

The assay is carried out for 30 minutes in the presence of 50 μM ATP using recombinant GST-ERK1 produced in E.Coli as substrate. Phosphorylation of the substrate is detected and quantified using HTRF reagents supplied by Cisbio. These consist of an anti-GST antibody conjugated to allophycocyanin (XL665) and an anti-phospho (Thr202/Tyr204) ERK antibody conjugated to europium-cryptate. These are used at a final concentration of 4 μg/ml and 0.84 μg/ml respectively. The anti-phospho antibody recognises ERK1 dually phosphorylated on Thr202 and Tyr204. When both antibodies are bound to ERK1 (i.e. when the substrate is phosphorylated), energy transfer from the cryptate to the allophycocyanin occurs following excitation at 340 nm, resulting in fluorescence being emitted that is proportional to the amount of phosphorylated substrate produced. Fluorescence is detected using a multiwell fluorimeter.

Compounds are diluted in DMSO prior to addition to assay buffer and the final DMSO concentration in the assay is 1%.

The $IC_{50}$ is defined as the concentration at which a given compound achieves 50% inhibition of control. $IC_{50}$ values are calculated using the XLfit software package (version 2.0.5).

Compounds of Examples 5-14 exhibited an $IC_{50}$ of less than 1 μM in the assay described in Example 1.

Example 2 bRaf Assay (MEK Activation Assay)

Constitutively activated bRaf mutant expressed in insect cells is used as source of enzymatic activity.

The assay is carried out for 30 minutes in the presence of 200 μM ATP using recombinant GST-MEK1 produced in E.Coli as substrate. Phosphorylation of the substrate is detected and quantified using HTRF, and reagents are supplied by Cisbio. These consist of an anti-GST antibody conjugated to allophycocyanin (XL665) and an anti-phospho (Ser217/Ser221) MEK antibody conjugated to europium-cryptate. The anti-phospho antibody recognises MEK dually phosphorylated on Ser217 and Ser221 or singly phosphorylated on Ser217. When both antibodies are bound to MEK (i.e. when the substrate is phosphorylated), energy transfer from the cryptate to the allophycocyanin occurs following excitation at 340 nm, resulting in fluorescence being emitted that is proportional to the amount of phosphorylated substrate produced. Fluorescence is detected using a multi-well fluorimeter.

Compounds are diluted in DMSO prior to addition to assay buffer and the final DMSO concentration in the assay is 1%.

The $IC_{50}$ is defined as the concentration at which a given compound achieves 50% inhibition of control. $IC_{50}$ values are calculated using the XLfit software package (version 2.0.5).

Example 3

Cell Proliferation Assay

Compounds are tested in a cell proliferation assay using the following cell lines:
HCT116 human colorectal carcinoma (ATCC)
A375 human malignant melanoma (ATCC)

Both cell lines are maintained in DMEM/F12 (1:1) media (Gibco) supplemented with 10% FCS at 37° C. in a 5% $CO_2$ humidified incubator.

Cells are seeded in 96-well plates at 2,000 cells/well and after 24 hours they are exposed to different concentrations of compounds in 0.83% DMSO. Cells are grown for a further 72 h, and an equal volume of CellTiter-Glo reagent (Promega) is added to each well. This lyses the cells and generates a luminescent signal proportional to the amount of ATP released (and therefore proportional to the number of cells in the well) that can be detected using a multi-well luminometer.

The $EC_{50}$ is defined as the concentration at which a given compound achieves 50% inhibition of control. $IC_{50}$ values are calculated using the XLfit software package (version 2.0.5).

In this assay, title compounds of Examples 5-11 and 13-14 exhibited an $EC_{50}$ of less than 10 µM in both cell lines. Title compound of Example 12 exhibited an $EC_{50}$ of less than 0.1 µM in the HCT116 cell line.

Example 4

Phospho-ERK Cell-Based Assay

Compounds are tested in a cell-based phospho-ERK ELISA using the following cell lines:
HCT116 human colorectal carcinoma (ATCC)
A375 human malignant melanoma (ATCC)

Both cell lines are maintained in DMEM/F12 (1:1) media (Gibco) supplemented with 10% FCS at 37° C. in a 5% $CO_2$ humidified incubator.

Cells are seeded in 96-well plates at 2,000 cells/well and after 24 h they are exposed to different concentrations of compounds in 0.83% DMSO. Cells are grown for a further 2 h or 24 h, fixed with formaldehyde (2% final) and permeabilised with methanol. Following blocking with TBST-3% BSA, fixed cells are incubated with primary antibody (anti-phospho ERK from rabbit) over-night at 4° C. Cells are incubated with Propidium Iodide (DNA fluorescent dye) and detection of cellular p-ERK is performed using an anti-rabbit secondary antibody conjugated to the fluorescent Alexa Fluor 488 dye (Molecular probes). The fluorescence is analysed using the Acumen Explorer (TTP Labtech), a laser-scanning microplate cytometer, and the Alexa Fluor 488 signal is normalised to the PI signal (proportional to cell number).

The $EC_{50}$ is defined as the concentration at which a given compound achieves a signal half way between the baseline and the maximum response. $EC_{50}$ values are calculated using the XLfit software package (version 2.0.5).

In this assay, title compounds of Examples 5-11 and 13-14 exhibited an $EC_{50}$ of less than 0.2 µM in both cell lines. Title compound of Example 12 exhibited an $EC_{50}$ of less than 0.2 µM in the HCT116 cell line.

Synthesis of Imidazo[1,5-a]Pyridines

8-Chloro-imidazo[1,5-a]pyridine-7-carboxylic acid methyl ester

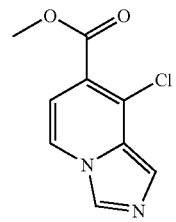

Step 1: 2,3-Dichloro-isonicotinic acid

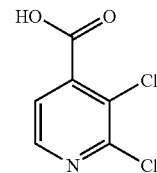

To a solution of diisopropylamine (7.0 mL, 50 mmol) in anhydrous THF (100 mL) at −25° C. was added a 1.6M solution of nBuLi in hexanes (31 mL, 50 mmol) dropwise under an inert atmosphere. The reaction mixture was then cooled to −78° C. and 2,3-dichloropyridine was added. The reaction mixture was stirred at −78° C. for 3 hours, then poured onto solid carbon dioxide and aged for 18 hours at room temperature. The mixture was diluted with water (100 mL) and washed with diethyl ether (3×40 mL) then cooled to 0° C., acidified with concentrated HCl (ca. 5 mL) and extracted with diethyl ether (3×50 mL). The combined organic extracts were dried ($Na_2SO_4$), filtered and concentrated to give the title compound as a white solid (7.7 g, 80%).
$^1$H NMR ($d_6$-DMSO, 400MHz) 8.49 (d, J=5.0 Hz, 1H), 7.72 (d, J=5.0 Hz, 1H).

Step 2: 2,3-Dichloro-isonicotinic acid methyl ester

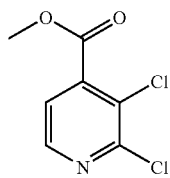

To a suspension of 2,3-dichloro-isonicotinic acid (7.7 g, 40 mmol) in dichloromethane (45 mL) were added DMF (0.1 mL) and oxalyl chloride (17.5 mL, 200 mmol). The reaction mixture was stirred at room temperature for 18 hours and then concentrated under reduced pressure. The resultant residue was azeotroped with toluene, then cooled to 0° C. and dissolved in methanol (135 mL). The mixture was allowed to warm to room temperature and then concentrated under reduced pressure to give a residue. The residue was dissolved in ethyl acetate and the resulting solution was washed with a saturated solution of sodium hydrogen carbonate, water and brine, dried ($Na_2SO_4$), filtered and concentrated to give the title compound as a colourless oil that crystallised on standing (7.9 g, 96%). $^1$H NMR ($CDCl_3$, 400MHz) 8.38 (d, J=5.0 Hz, 1H), 7.52 (d, J=5.0 Hz, 1H), 3.99 (s, 3H).

Step 3: 3-Chloro-2-cyano-isonicotinic acid methyl ester

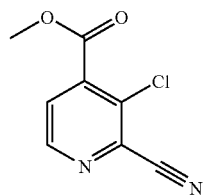

A microwave vial was charged with 2,3-dichloro-isonicotinic acid methyl ester (7.6 g, 36.9 mmol), zinc cyanide (4.75 g, 40.6 mmol), tetrakis(triphenylphosphine)palladium (1.0 g, 0.9 mmol) and DMF (37 mL), then capped, evacuated and backfilled with nitrogen. The reaction solution was subjected to microwave irradiation, heating at 190° C. for 20 minutes, then filtered through a pad of Celite® which was washed further with ethyl acetate. The resulting mixture was washed with water, followed by a saturated solution of sodium hydrogen carbonate, then brine, dried ($Na_2SO_4$), filtered and concentrated in vacuo. The resultant residue was subjected to column chromatography (Si-PPC, gradient 0% to 100%, ethyl acetate in cyclohexane) to give the title compound as a white solid (3.1 g, 43%). $^1$H NMR ($CDCl_3$, 400 MHz) 8.70 (d, J=5.0 Hz, 1H), 7.87 (d, J=5.0 Hz, 1H), 4.01 (s, 3H).

Step 4: 3-Chloro-2-formylaminomethyl-isonicotinic acid methylester

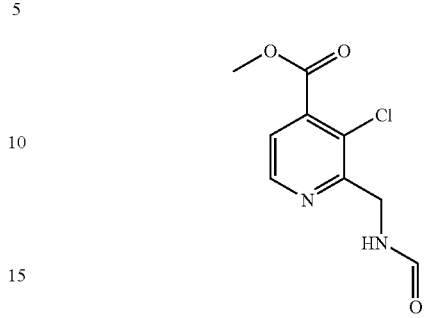

A mixture of 3-chloro-2-cyano-isonicotinic acid methyl ester (2.9 g, 14.8 mmol) and 10% palladium on charcoal (293 mg) in acetic acid (65 mL) was degassed and backfilled with hydrogen three times. The reaction mixture was stirred at room temperature under an atmosphere of hydrogen (1 bar) for 18 hours and then filtered. The filtrate was concentrated under reduced pressure to give a residue which was dissolved in methanol and loaded onto a 50 g Isolute® SCX-2 cartridge, eluted with methanol followed by a 2M solution of ammonia in methanol. The appropriate fractions were combined and concentrated under reduced pressure to give a residue. The residue was dissolved in a mixture of formic acid (40 mL) and acetic anhydride (8 mL), which was stirred at room temperature for 30 minutes. The solvents were removed under reduced pressure to give a residue which was dissolved in dichloromethane. The resulting solution was washed with a saturated solution of sodium hydrogen carbonate, the aqueous layer was separated and extracted twice with dichloromethane. The combined organic extracts were passed through a phase separator and concentrated under reduced pressure to give a residue that was subjected to column chromatography (Si-PPC, gradient 0% to 10%, methanol in dichloromethane). The title compound was obtained as a white solid (1.5 g, 44%). LCMS (method B): $R_T$=2.15 min, $[M+H]^+$=229.

Step 5: 8-Chloro-imidazo[1,5-a]pyridine-7-carboxylic acid methyl ester

A mixture of 3-chloro-2-formylaminomethyl-isonicotinic acid methyl ester (1.5 g, 6.6 mmol) and phosphorous oxychloride (1.3 mL, 14.2 mmol) in toluene (80 mL) was stirred at 90° C. for 15 minutes, then cooled to room temperature and concentrated under reduced pressure. The residue was partitioned between ethyl acetate and a saturated solution of sodium bicarbonate. The organic layer was separated and washed with water and brine, dried ($Na_2SO_4$), filtered and concentrated to give the title compound as a pale yellow solid (1.3 g, 93%). LCMS (method B): $R_T$=2.38 min, $[M+H]^+$=211.

8-(4-Cyclopropyl-2-fluoro-phenylamino)-imidazo[1,5-a]pyridine-7-carboxylic acid

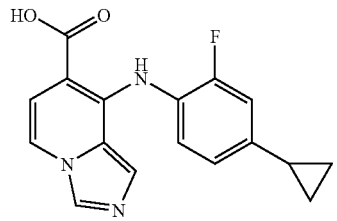

Step 1: 8-(4-Cyclopropyl-2-fluoro-phenylamino)-imidazo[1,5-a]pyridine-7-carboxylic acid methyl ester

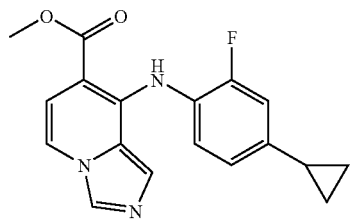

A suspension of 8-chloro-imidazo[1,5-a]pyridine-7-carboxylic acid methyl ester (105 mg, 0.50 mmol), 4-cyclopropyl-2-fluoroaniline (101 mg, 0.60 mmol), $Pd_2dba_3$ (18 mg, 0.02 mmol), 2-dicyclohexylphosphino-2',6'-diisopropoxybiphenyl (37 mg, 0.08 mmol) and $K_3PO_4$ (148 mg, 0.70 mmol) in toluene (2 mL) was degassed and then heated to 100° C. for 24 hours. The reaction mixture was then cooled to room temperature and diluted with ethyl acetate. The resultant solution was washed with water and brine, then loaded onto a 10 g Isolute® SCX-2 cartridge which was eluted with methanol followed by a 2M solution of ammonia in methanol. The appropriate fractions were combined and concentrated. The resultant residue was subjected to flash chromatography (Si-PPC, gradient 0% to 10%, ethyl acetate in dichloromethane) to afford the title compound as a yellow oil (68 mg, 42%). LCMS (method B): $R_T$=3.45 min, [M+H]$^+$=326.

Step 2: 8-(4-Cyclopropyl-2-fluoro-phenylamino)-imidazo[1,5-a]pyridine-7-carboxylic acid A suspension of 8-(4-cyclopropyl-2-fluoro-phenylamino)-imidazo[1,5-a]pyridine-7-carboxylic acid methyl ester (0.28 g, 0.86 mmol) and 1M NaOH (1.03 mL, 1.03 mmol) in IMS (5 mL) was heated to 65° C. for 5 hours. The reaction mixture was then cooled to room temperature and 1M HCl was added to adjust pH to 2. The precipitate formed was filtered off and dried in a drying pistol at 40° C. for 18 hours to afford the title compound as a cream solid (0.22 g, 81%). LCMS (method B): $R_T$=2.84 min, [M+H]$^+$=312.

Example 5

8-(4-Cyclopropyl-2-fluoro-phenylamino)-imidazo[1,5-a]pyridine-7-carboxylic acid amide

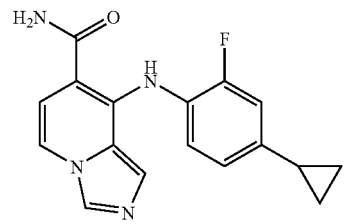

To a solution of 8-(4-cyclopropyl-2-fluoro-phenylamino)-imidazo[1,5-a]pyridine-7-carboxylic acid methyl ester (23 mg, 0.07 mmol) in IMS (1.0 mL) was added a 1.0 M aqueous solution of sodium hydroxide (0.10 mL, 0.10 mmol). The reaction mixture was heated to 65° C. for 1 hour and then cooled to room temperature and concentrated in vacuo. The resulting residue was azeotroped with toluene, and then dissolved in DMF (1 mL). Ammonium chloride (7 mg, 0.13 mmol), N-N-diisopropylethylamine (47 uL, 0.27 mmol) and HATU (51 mg, 0.13 mmol) were added sequentially, before the reaction mixture was stirred for 18 hours at room temperature. The reaction mixture was then diluted with methanol and loaded onto an Isolute® SCX-2 cartridge (5 g). The cartridge was then washed with methanol and the desired product was subsequently eluted using 2M $NH_3$ in MeOH. The eluent was collected and concentrated to give a residue. The residue was subjected to flash chromatography (Si-PPC, gradient 0% to 5%, methanol in dichloromethane) to afford the title compound as a pale yellow solid (5 mg, 23%). LCMS (method A): $R_T$=6.64 min, [M+H]$^+$=311. $^1$H NMR (CD$_3$OD) 8.18 (1H, d, J=0.88 Hz), 7.64 (1H, dd, J=7.40, 0.97 Hz), 7.13 (1H, t, J=8.28 Hz), 6.93-6.86 (3 H, m), 6.35 (1H, s), 1.98-1.90 (1 H, m), 1.05-0.97 (2 H, m), 0.73-0.68 (2H, m).

Example 6

8-(4-Cyclopropyl-2-fluoro-phenylamino)-imidazo[1,5-a]pyridine-7-carboxylic acid (2-hydroxy-ethoxy)-amide

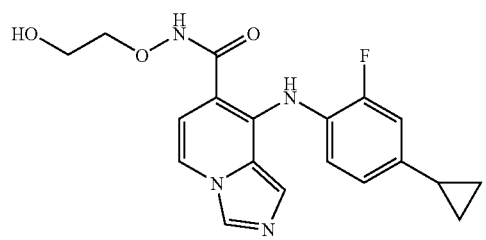

Step 1: 8-(4-Cyclopropyl-2-fluoro-phenylamino)-imidazo[1,5-a]pyridine-7-carboxylic acid (2-vinyloxy-ethoxy)-amide

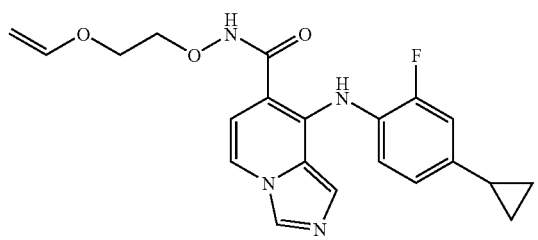

To a solution of 8-(4-cyclopropyl-2-fluoro-phenylamino)-imidazo[1,5-a]pyridine-7-carboxylic acid methyl ester (68 mg, 0.21 mmol) in IMS (2.5 mL) was added a 1.0 M aqueous solution of sodium hydroxide (0.25 mL, 0.25 mmol). The reaction mixture was heated at 65° C. for 1 hour and then cooled to room temperature and concentrated in vacuo. The resulting residue was azeotroped with toluene, and then suspended in THF (4 mL). 042-Vinyloxy-ethyl)-hydroxylamine (43 mg, 0.42 mmol), N-N-diisopropylethylamine (0.14 mL, 0.84 mmol), EDCI (81 mg, 0.42 mmol) and HOBt (57 mg, 0.42 mmol) were then added sequentially, before the reaction mixture was stirred for 18 hours at room temperature. The reaction mixture was then diluted with ethyl acetate and washed with water, a saturated aqueous solution of sodium bicarbonate and brine before being dried ($Na_2SO_4$), filtered and concentrated in vacuo. The resultant residue was subjected to flash chromatography (Si-PPC, gradient 0% to 5%, methanol in dichloromethane) to afford the title compound as a pale yellow oil (56 mg, 67%). LCMS (method B): $R_T$=3.02 min, $[M+H]^+$=397.

Step 2: 8-(4-Cyclopropyl-2-fluoro-phenylamino)-imidazo[1,5-a]pyridine-7-carboxylic acid (2-hydroxy-ethoxy)-amide 8-(4-Cyclopropyl-2-fluoro-phenylamino)-imidazo[1,5-a]pyridine-7-carboxylic acid (2-vinyloxy-ethoxy)-amide (56 mg, 0.14 mmol) was dissolved in methanol and loaded onto an Isolute® SCX-2 cartridge (5 g). The cartridge was then washed with methanol and the desired product was subsequently eluted using 2M $NH_3$ in MeOH. The eluent was collected and concentrated to give a residue. The residue was subjected to flash chromatography (Si-PPC, gradient 0% to 20%, methanol in dichloromethane) to afford the title compound as a pale yellow solid (37 mg, 71%). LCMS (method A): $R_T$=6.40 min, $[M+H]^+$=371. $^1$H NMR ($CH_3OH-d_4$): 8.20 (1 H, d, J=0.71 Hz), 7.67-7.65 (1 H, m), 7.17-7.11 (1 H, m), 6.94-6.87 (2H, m), 6.73 (1 H, d, J=7.38 Hz), 6.39 (1 H, s), 4.00-3.97 (2 H, m), 3.75-3.72 (2 H, m), 1.98-1.89 (1 H, m), 1.04-0.98 (2 H, m), 0.73-0.68 (2 H, m).

Example 7

8-(2-Fluoro-4-methylsulfanyl-phenylamino)-imidazo[1,5-a]pyridine-7-carboxylic acid (2-hydroxy-ethoxy)-amide

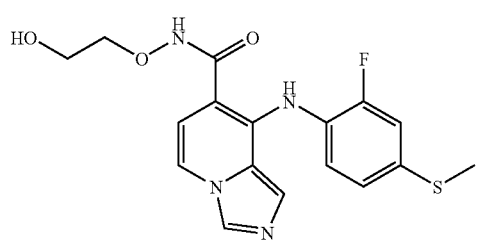

Step 1: 8-(2-Fluoro-4-methylsulfanyl-phenylamino)-imidazo[1,5-a]pyridine-7-carboxylic acid methyl ester

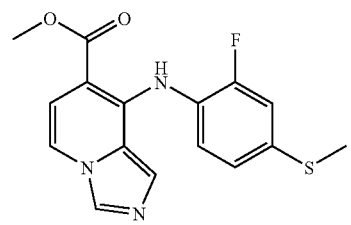

A suspension of 8-chloro-imidazo[1,5-a]pyridine-7-carboxylic acid methyl ester (223 mg, 1.06 mmol), 2-fluoro-4-methylsulfanyl-phenylamine (200 mg, 1.27 mmol), $Pd_2dba_3$ (39 mg, 0.04 mmol), 2-dicyclohexylphosphino-2',6'-diisopropoxybiphenyl (79 mg, 0.17 mmol) and $K_3PO_4$ (315 mg, 1.48 mmol) in toluene (4 mL) was degassed and then heated at 100° C. for 18 hours. The reaction mixture was then cooled to room temperature and diluted with ethyl acetate. The resultant mixture was washed with water followed by brine, before being loaded onto a 10 g Isolute® SCX-2 cartridge which was eluted with methanol, and then a 2M solution of ammonia in methanol. The appropriate fractions were combined and concentrated in vacuo to give a residue. The residue was subjected to flash chromatography (Si-PPC, gradient 0% to 10%, ethyl actetate in dichloromethane) to afford the title compound as a yellow oil (136 mg, 39%). LCMS (method B): $R_T$=3.26 min, $[M+H]^+$=332.

Step 2: 8-(2-Fluoro-4-methylsulfanyl-phenylamino)-imidazo[1,5-a]pyridine-7-carboxylic acid (2-vinyloxy-ethoxy)-amide

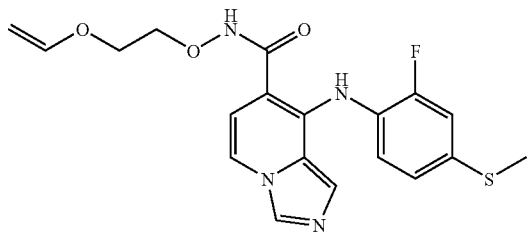

To a solution of 8-(2-fluoro-4-methylsulfanyl-phenylamino)-imidazo[1,5-a]pyridine-7-carboxylic acid methyl ester (136 mg, 0.41 mmol) in IMS (10 mL) was added a 1.0 M aqueous solution of sodium hydroxide (0.82 mL, 0.82 mmol). The reaction mixture was heated at 65° C. for 1 hour and then cooled to room temperature and concentrated in vacuo. The resultant residue was azeotroped with toluene, and then suspended in THF (10 mL). O-(2-Vinyloxy-ethyl)-hydroxylamine (84 mg, 0.82 mmol), N-N-diisopropylethylamine (0.28 mL, 1.64 mmol), EDCI (157 mg, 0.82 mmol) and HOBt (111 mg, 0.82 mmol) were then added sequentially, before the reaction mixture was stirred for 18 hours at room temperature. The reaction mixture was then diluted with ethyl acetate and washed with water, a saturated aqueous solution of sodium bicarbonate and brine, dried (Na$_2$SO$_4$), filtered and concentrated. The resultant residue was subjected to flash chromatography (Si-PPC, gradient 0% to 100%, ethyl acetate in dichloromethane) to afford the title compound as a pale yellow oil (160 mg, 97%). LCMS (method B): R$_T$=2.91 min, [M+H]$^+$=403.

Step 3: 8-(2-Fluoro-4-methylsulfanyl-phenylamino)-imidazo[1,5-a]pyridine-7-carboxylic acid (2-hydroxy-ethoxy)-amide 8-(2-Fluoro-4-methylsulfanyl-phenylamino)-imidazo[1,5-a]pyridine-7-carboxylic acid (2-vinyloxy-ethoxy)-amide (160 mg, 0.40 mmol) was dissolved in methanol and loaded onto an Isolute® SCX-2 cartridge (10 g). The cartridge was then washed with methanol and the desired product was subsequently eluted using 2M NH$_3$ in MeOH. The eluent was collected and concentrated to give a residue, which was subjected to flash chromatography (Si-PPC, gradient 0% to 10%, methanol in dichloromethane) to afford the title compound as a pale yellow solid (77 mg, 51%). LCMS (method A): R$_T$=5.96 min, [M+H]$^+$=377. $^1$H NMR (DMSO-d$_6$) 11.54 (1 H, s), 10.51 (1 H, s), 8.29 (1 H, d, J=0.80 Hz), 7.80 (1 H, dd, J=7.37, 0.94 Hz), 7.24-7.16 (2 H, m), 7.06 (1 H, dd, J=8.38, 2.11 Hz), 6.80-6.74 (1 H, m), 6.39 (1 H, s), 4.70 (1 H, s), 3.86 (2 H, t, J=4.95 Hz), 3.57 (2 H, t, J=4.95 Hz), 2.49 (3 H, s).

Example 8

8-(2-Fluoro-4-iodo-phenylamino)-imidazo[1,5-a]pyridine-7-carboxylic acid (2-hydroxy-ethoxy)-amide

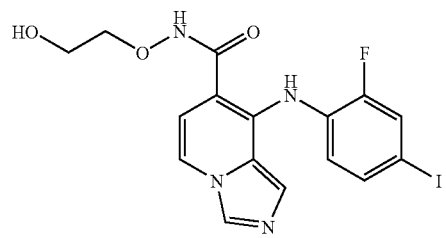

Step 1: 8-(4-Bromo-2-fluoro-phenylamino)-imidazo[1,5-a]pyridine-7-carboxylic acid methyl ester

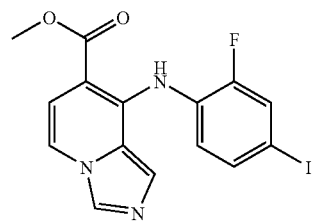

A suspension of 8-chloro-imidazo[1,5-a]pyridine-7-carboxylic acid methyl ester (500 mg, 2.38 mmol), 4-bromo-2-fluoroaniline (543 mg, 2.86 mmol), Pd$_2$dba$_3$ (110 mg, 0.12 mmol), 2-dicyclohexylFphosphino-2',6'-diisopropoxybiphenyl (224 mg, 0.48 mmol) and K$_3$PO$_4$ (710 mg, 3.33 mmol) in toluene (10 mL) was degassed and then heated at 100° C. for 18 hours. The reaction mixture was then cooled to room temperature, diluted with ethyl acetate and filtered. The filtrate was washed with water and brine, then loaded onto a 10 g Isolute® SCX-2 cartridge which was eluted with methanol and then a 2M solution of ammonia in methanol. The appropriate fractions were combined and concentrated in vacuo. The resultant residue was subjected to flash chromatography (Si-PPC, gradient 0% to 20%, ethyl actetate in DCM) to afford the title compound as a yellow oil (240 mg, 28%). LCMS (method B): R$_T$=3.40 min, [M+H]$^+$=364/366.

Step 2: 8-(2-Fluoro-4-iodo-phenylamino)-imidazo[1,5-a]pyridine-7-carboxylic acid methyl ester A mixture of 8-(4-bromo-2-fluoro-phenylamino)-imidazo[1,5-a]pyridine-7-carboxylic acid methyl ester (235 mg, 0.65 mmol), copper (I) iodide (6 mg, 0.03 mmol), sodium iodide (195 mg, 1.3 mmol) and trans-N,N'-dimethyl-1,2-cyclohexane diamine (0.01 mL, 0.06 mmol) in 1,4-dioxane (1.0 mL) was heated at 110° C. for 26 hours under an argon atmosphere. The reaction mixture was cooled to room temperature, diluted with methanol and loaded onto an Isolute® SCX-2 cartridge (10 g). The cartridge was then washed with methanol and the desired product was subsequently eluted using 2M $NH_3$ in MeOH. The eluent was collected and concentrated to give a residue. The residue was subjected to flash chromatography (Si-PPC, gradient 0% to 20%, ethyl acetate in dichloromethane) to afford the title compound as a pale yellow solid (182 mg, 67%). LCMS (method B): $R_T$=3.45 min, $[M+H]^+$=412.

Step 3: 8-(2-Fluoro-4-iodo-phenylamino)-imidazo[1,5-a]pyridine-7-carboxylic acid (2-vinyloxy-ethoxy)-amide

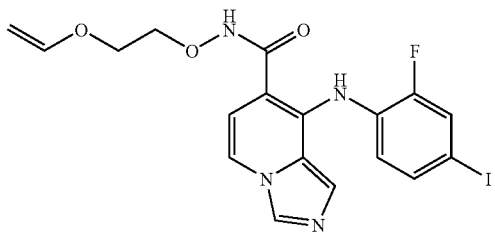

To a solution of 8-(2-fluoro-4-iodo-phenylamino)-imidazo[1,5-a]pyridine-7-carboxylic acid methyl ester (200 mg, 0.49 mmol) in IMS (10 mL) was added a 1.0 M aqueous solution of sodium hydroxide (1.0 mL, 1.0 mmol). The reaction mixture was heated at 65° C. for 2 hours and then cooled to room temperature and concentrated in vacuo. The resulting residue was azeotroped with toluene, and then suspended in THF (10 mL). O-(2-Vinyloxy-ethyl)-hydroxylamine (103 mg, 1.0 mmol), N-N-diisopropylethylamine (0.34 mL, 1.96 mmol), EDCI (192 mg, 1.0 mmol) and HOBt (135 mg, 1.0 mmol) were then added sequentially before the reaction mixture was stirred 18 hours at room temperature. The reaction mixture was then diluted with ethyl acetate and washed with water followed by a saturated aqueous solution of sodium bicarbonate and then brine, dried ($Na_2SO_4$), filtered and concentrated in vacuo. The resultant residue was subjected to flash chromatography (Si-PPC, gradient 0% to 100%, ethyl acetate in dichloromethane) to afford the title compound as a pale yellow oil (151 mg, 64%). LCMS (method B): $R_T$=3.05 min, $[M+H]^+$=483.

Step 4: 8-(2-Fluoro-4-iodo-phenylamino)-imidazo[1,5-a]pyridine-7-carboxylic acid (2-hydroxy-ethoxy)-amide 8-(2-Fluoro-4-iodo-phenylamino)-imidazo[1,5-a]pyridine-7-carboxylic acid (2-vinyloxy-ethoxy)-amide (151 mg, 0.31 mmol) was dissolved in methanol and loaded onto an Isolute® SCX-2 cartridge (10 g). The cartridge was then washed with methanol and the desired product was subsequently eluted using 2M $NH_3$ in MeOH. Appropriate fractions were combined and concentrated to give a residue that was subjected to flash chromatography (Si-PPC, gradient 0% to 10%, methanol in dichloromethane) to afford the title compound as a pale yellow solid (115 mg, 81%). LCMS (method A): $R_T$=6.36 min, $[M+H]^+$=457. $^1$H NMR ($CD_3OD$): 8.27 (1H, d, J=0.85 Hz), 7.80-7.77 (1H, m), 7.57-7.53 (1H, m), 7.49-7.46 (1H, m), 6.95 (1H, t, J=8.48 Hz), 6.76 (1H, d, J=7.37 Hz), 6.68 (1H, s), 4.00-3.94 (2H, m), 3.75-3.71 (2H, m).

Example 9

8-(4-Cyclopropyl-2-fluoro-phenylamino)-imidazo[1,5-a]pyridine-7-carboxylic acid ((S)-2-hydroxy-propoxy)-amide

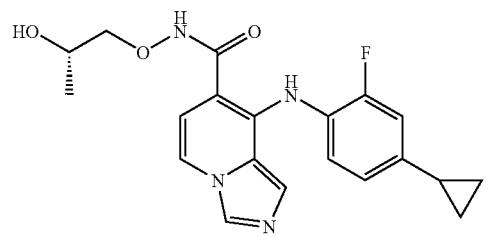

A suspension of 8-(4-cyclopropyl-2-fluoro-phenylamino)-imidazo[1,5-a]pyridine-7-carboxylic acid (0.11 g, 0.35 mmol), EDCI (0.081 g, 0.42 mmol), HOBt (0.057 g, 0.42 mmol), DIPEA (0.085 mL, 0.88 mmol) and (S)-1-aminooxypropan-2-ol hydrochloride (0.05 g, 0.39 mmol) in DMF (1.5 mL) was stirred at room temperature for 18 hours. The reaction mixture was partitioned between DCM (5 mL) and saturated aqueous $NaHCO_3$ (5 mL). The organic layer was washed with water (5 mL), followed by brine (5 mL), then dried ($MgSO_4$), filtered and concentrated in vacuo. The resultant residue was subjected to flash chromatography (Si-PPC, gradient 0% to 60%, ethyl actetate in DCM) to give a yellow sticky solid, which was further purified by preparative HPLC (Gemini 5 micron $C_{18}$ 250×21.20 mm column, 0.1% formic acid, gradient acetonitrile/water, 5 to 98%, ramp time 20 minutes) to afford the title compound as a yellow solid (38 mg, 27%). LCMS (method A): $R_T$=6.87 min, $[M+H]^+$=385. $^1$H NMR (DMSO-$d_6$) 10.54 (1H, s), 8.27 (1H, s), 7.76 (1H, dd, J=7.37, 0.93 Hz), 7.14 (1H, t, J=8.37 Hz), 6.98 (1H, dd, J=11.87, 1.95 Hz), 6.95-6.89 (1H, m), 6.76 (1H, d, J=7.33 Hz), 6.27 (1H, s), 3.89-3.79 (1H, m), 3.72-3.62 (2H, m), 1.99-1.90 (1H, m), 1.04 (3H, d, J=6.34 Hz), 0.99-0.93 (2H, m), 0.76-0.67 (2H, m).

Example 10

8-(4-Cyclopropyl-2-fluoro-phenylamino)-imidazo[1,5-a]pyridine-7-carboxylic acid (2-hydroxy-1,1-dimethyl-ethoxy)-amide

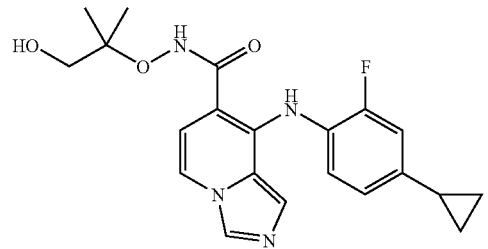

A suspension of 8-(4-cyclopropyl-2-fluoro-phenylamino)-imidazo[1,5-a]pyridine-7-carboxylic acid (0.11 g, 0.35 mmol), EDCI (0.081 g, 0.42 mmol), HOBt (0.057 g, 0.42 mmol), DIPEA (0.085 mL, 0.88 mmol) and 2-aminooxy-2-methyl-propan-1-ol hydrochloride (0.055 g, 0.39 mmol) in DMF (1.5 mL) was stirred at room temperature for 18 hours. The reaction mixture was partitioned between DCM (5 mL) and saturated aqueous NaHCO₃ (5 ml). The organic layer was washed with water (5 mL), followed by brine (5 mL), then dried (MgSO₄), filtered and concentrated in vacuo. The resultant residue was subjected to flash chromatography (Si-PPC, gradient 0% to 40%, ethyl actetate in DCM) to give a yellow solid, which was further purified by preparative HPLC (Gemini 5 micron C$_{18}$ 250×21.20 mm column, 0.1% formic acid, gradient acetonitrile/water, 5 to 98%, ramp time 20 minutes) to afford the title compound as a yellow solid (11 mg, 8%). LCMS (method A): R$_T$=7.57 min, [M+H]⁺=399. ¹H NMR (DMSO-d₆): 10.37 (1H, s), 8.28 (1H, s), 7.79 (1H, dd, J=7.35, 0.95 Hz), 7.14 (1H, s), 7.02-6.93 (1H, m), 6.91 (1H, d, J=8.28 Hz), 6.82 (1H, s), 6.27 (1H, s), 1.99-1.90 (1H, m), 1.15 (6H, s), 0.99-0.92 (2H, m), 0.73-0.67 (2H, m).

Example 11

8-(4-Bromo-2-fluoro-phenylamino)-imidazo[1,5-a]pyridine-7-carboxylic acid (2-hydroxy-ethoxy)-amide

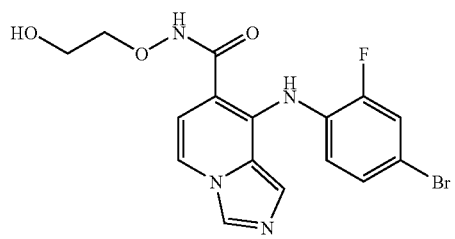

Step 1: 8-(4-Bromo-2-fluoro-phenylamino)-imidazo[1,5-a]pyridine-7-carboxylic acid (2-vinyloxy-ethoxy)-amide

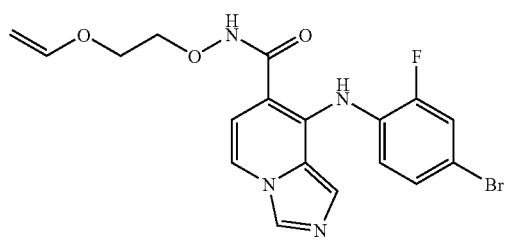

To a solution of 8-(4-bromo-2-fluoro-phenylamino)-imidazo[1,5-a]pyridine-7-carboxylic acid methyl ester (50 mg, 0.14 mmol) in IMS (3 mL) was added a 1.0 M aqueous solution of sodium hydroxide (0.3 mL, 0.3 mmol). The reaction mixture was heated at 65° C. for 2 hours and then cooled to room temperature and concentrated in vacuo. The resulting residue was azeotroped with toluene, and then suspended in THF (3 mL). O-(2-Vinyloxy-ethyl)-hydroxylamine (29 mg, 0.28 mmol), N-N-diisopropylethylamine (0.10 mL, 0.56 mmol), EDCI (54 mg, 0.28 mmol) and HOBt (38 mg, 0.28 mmol) were then added sequentially before the reaction mixture was stirred 18 hours at room temperature. The reaction mixture was then diluted with ethyl acetate and washed with water followed by a saturated aqueous solution of sodium bicarbonate and brine. The organic layer was isolated, dried (Na₂SO₄), filtered and concentrated in vacuo. The resultant residue was subjected to flash chromatography (Si-PPC, gradient 0% to 100%, ethyl acetate in dichloromethane) to afford the title compound as a pale yellow oil (40 mg, 65%). LCMS (method B): R$_T$=2.98 min, [M+H]⁺=435/437.

Step 2: 8-(4-Bromo-2-fluoro-phenylamino)-imidazo[1,5-a]pyridine-7-carboxylic acid (2-hydroxy-ethoxy)-amide 8-(4-Bromo-2-fluoro-phenylamino)-imidazo[1,5-a]pyridine-7-carboxylic acid (2-vinyloxy-ethoxy)-amide (40 mg, 0.09 mmol) was dissolved in methanol and loaded onto an Isolute® SCX-2 cartridge (5 g). The cartridge was then washed with methanol and the desired product was subsequently eluted using 2M NH₃ in MeOH. Appropriate fractions were combined and concentrated to give a residue that was subjected to flash chromatography (Si-PPC, gradient 0% to 20%, methanol in dichloromethane) to afford the title compound as a pale yellow solid (11 mg, 29%). LCMS (method A): R$_T$=6.06 min, [M+H]⁺=409/411. ¹H NMR (CD₃OD): 8.27 (1 H, d, J=0.85 Hz), 7.79 (1 H, dd, J=7.39, 0.97 Hz), 7.42 (1 H, dd, J=10.00, 2.19 Hz), 7.31 (1 H, ddd, J=8.53, 2.20, 1.19 Hz), 7.12 (1 H, t, J=8.60 Hz), 6.79-6.73 (1 H, m), 6.65 (1 H, s), 3.97 (2 H, t, J=4.69 Hz), 3.73 (2 H, t, J=4.68 Hz).

Example 12

8-(4-Bromo-2-fluoro-phenylamino)-imidazo[1,5-a]pyridine-7-carboxylic acid ((S)-2-hydroxy-propoxy)-amide

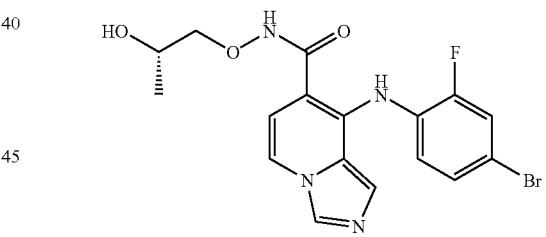

To a solution of 8-(4-bromo-2-fluoro-phenylamino)-imidazo[1,5-a]pyridine-7-carboxylic acid methyl ester (587 mg, 1.61 mmol) in IMS (20 mL) was added a 1.0 M aqueous solution of sodium hydroxide (1.7 mL, 1.7 mmol). The reaction mixture was heated at 65° C. for 2 hours and then cooled to room temperature and concentrated in vacuo. The resulting residue was azeotroped with toluene, and then suspended in dioxane (15 mL). EDCI (614 mg, 3.2 mmol) and HOBt (432 mg, 3.2 mmol) were then added before the reaction mixture was stirred for 30 min at room temperature. (S)-1-Aminooxy-propan-2-ol hydrochloride (408 mg, 3.20 mmol) and N-N-diisopropylethylamine (1.1 mL, 6.44 mmol) were then added sequentially before the reaction mixture was stirred for 18 hours at room temperature. The reaction mixture was then concentrated under reduced pressure. The resultant residue was taken up in ethyl acetate, then washed with water followed by a saturated aqueous solution of sodium bicarbonate and brine, dried (Na₂SO₄), filtered and concentrated in vacuo.

The resultant residue was subjected to flash chromatography (Si-PPC, gradient 0% to 10%, methanol in dichloromethane). The appropriate fractions were combined and concentrated to give a residue that was subjected to HPLC (Gemini 5 micron $C_{18}$ 250×21.20 mm column, 0.1% formic acid, acetonitrile in water, gradient 5% to 85%, ramp time 20 minutes) to afford the title compound as a pale yellow solid (180 mg, 26%). LCMS (method A): $R_T$=6.55 min, $[M+H]^+$=423/425. $^1$H NMR (CDCl$_3$): 10.46 (1H, s), 8.75 (1H, s), 7.99 (1H, s), 7.39 (1H, d, J=7.36 Hz), 7.32 (1H, dd, J=9.31, 2.15 Hz), 7.28 (1H, d, J=8.83 Hz), 7.12 (1H, t, J=8.38 Hz), 6.63 (1H, s), 6.46 (1H, d, J=7.33 Hz), 4.10-4.01 (1H, m), 3.93 (1H, dd, J=11.43, 2.28 Hz), 3.70 (1H, t, J=10.42 Hz), 1.14 (3H, d, J=6.47 Hz).

Example 13

8-(4-Bromo-2-chloro-phenylamino)-imidazo[1,5-a] pyridine-7-carboxylic acid (2-hydroxy-ethoxy)-amide

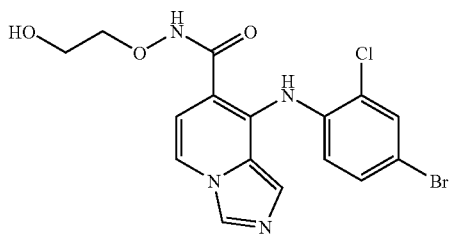

Step 1: 8-(4-Bromo-2-chloro-phenylamino)-imidazo [1,5-a]pyridine-7-carboxylic acid methyl ester

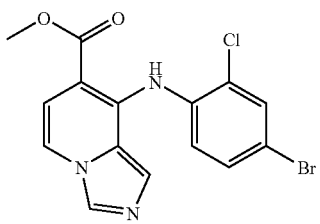

A suspension of 8-chloro-imidazo[1,5-a]pyridine-7-carboxylic acid methyl ester (300 mg, 1.43 mmol), 4-bromo-2-chloroaniline (354 mg, 1.72 mmol), Pd$_2$dba$_3$ (65 mg, 0.07 mmol), 2-dicyclohexylphosphino-2',6'-diisopropoxybiphenyl (131 mg, 0.28 mmol) and K$_3$PO$_4$ (424 mg, 2.00 mmol) in toluene (5 ml) was degassed and then heated at 110° C. for 18 hours. The reaction mixture was then cooled to room temperature and diluted with ethyl acetate. The resultant mixture was washed with water and brine, then loaded onto a 10 g Isolute® SCX-2 cartridge which was eluted with methanol and then a 2M solution of ammonia in methanol. The appropriate fractions were combined and concentrated in vacuo. The resultant residue was subjected to flash chromatography (Si-PPC, gradient 0% to 100%, ethyl actetate in DCM) to afford the title compound as a yellow oil (271 mg, 50%). LCMS (method B): $R_T$=3.65 min, $[M+H]^+$=381/383.

Step 2: 8-(4-Bromo-2-chloro-phenylamino)-imidazo [1,5-a]pyridine-7-carboxylic acid (2-vinyloxy-ethoxy)-amide

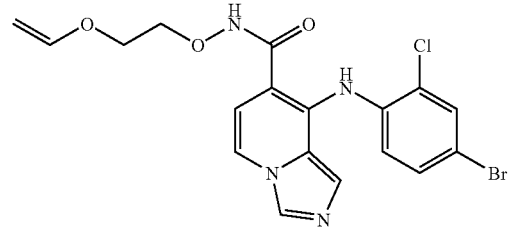

To a solution of 8-(4-bromo-2-chloro-phenylamino)-imidazo[1,5-a]pyridine-7-carboxylic acid methyl ester (271 mg, 0.71 mmol) in IMS (10 mL) was added a 1.0 M aqueous solution of sodium hydroxide (0.8 mL, 0.8 mmol). The reaction mixture was heated at 65° C. for 1 hour and then cooled to room temperature and concentrated in vacuo. The resulting residue was azeotroped with toluene, and then suspended in THF (10 mL). O-(2-Vinyloxy-ethyl)-hydroxylamine (89 mg, 0.87 mmol), N-N-diisopropylethylamine (0.30 mL, 1.73 mmol), EDCI (166 mg, 0.87 mmol) and HOBt (117 mg, 0.87 mmol) were then added sequentially before the reaction mixture was stirred 18 hours at room temperature. The reaction mixture was then diluted with ethyl acetate and washed with water followed by a saturated aqueous solution of sodium bicarbonate and then brine. The isolated organic layer was dried (Na$_2$SO$_4$), filtered and concentrated in vacuo to afford the title compound as a pale yellow solid (210 mg, 65%). LCMS (method B): $R_T$=3.17 min, $[M+H]^+$=451/453.

Step 3: 8-(4-Bromo-2-chloro-phenylamino)-imidazo [1,5-a]pyridine-7-carboxylic acid (2-hydroxy-ethoxy)-amide 8-(4-Bromo-2-chloro-phenylamino)-imidazo[1,5-a]pyridine-7-carboxylic acid (2-vinyloxy-ethoxy)-amide (196 mg, 0.43 mmol) was dissolved in methanol and loaded onto an Isolute® SCX-2 cartridge (10 g). The cartridge was then washed with methanol and the desired product was subsequently eluted using 2M NH$_3$ in MeOH. Appropriate fractions were combined and concentrated to give a residue that was subjected to flash chromatography (Si-PPC, gradient 0% to 10%, methanol in dichloromethane). The appropriate fractions were combined and concentrated to give a residue that was subjected to HPLC (Preparative C$_{18}$ column, 0.1% formic acid, acetonitrile in water, gradient 5% to 98%, ramp time 20 minutes) to afford the title compound as a pale yellow solid (43 mg, 23%). LCMS (method A): $R_T$=6.71 min, $[M+H]^+$=425/427. $^1$H NMR (DMSO-d$_6$): 11.68 (1H, s), 10.46 (1H, s), 8.35 (1H, d, J=0.79 Hz), 7.95 (1H, d, J=7.36 Hz), 7.78 (1H, d, J=2.27 Hz), 7.42 (1H, dd, J=8.62, 2.29 Hz), 7.01 (1H, d, J=8.63 Hz), 6.79 (1H, d, J=7.35 Hz), 6.56 (1H, s), 4.69 (1H, s), 3.87 (2H, t, J=4.89 Hz), 3.57 (2H, m).

Example 14

8-(4-Cyclobutyl-2-fluoro-phenylamino)-imidazo[1,5-a]pyridine-7-carboxylic acid (2-hydroxy-ethoxy)-amide

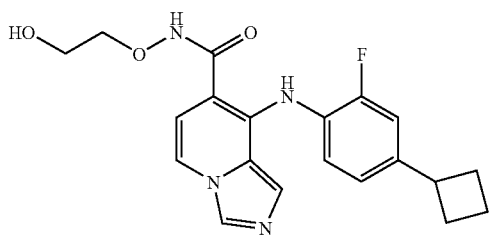

Step 1: 4-cyclobutyl-2-fluoro-nitrobenzene

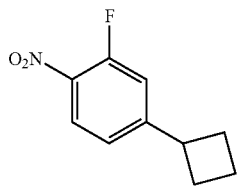

A solution of trifluoro-methanesulfonic acid 3-fluoro-4-nitro-phenyl ester (1.8 g, 6.2 mmol), cyclobutyl boronic acid (0.78 g, 7.5 mmol), Pd(dppf)Cl$_2$ (0.40 g, 0.5 mmol), and 2M aqueous cesium carbonate (aq) (5 mL, 9.9 mmol) in toluene (10 ml) was degassed with argon for 10 minutes and then heated to 90° C. for 2.5 hours. The reaction mixture was then cooled to room temperature and filtered through hyflo®. The reaction mixture was partitioned between ethyl acetate (70 mL) and water (70 mL). The organic layer was isolated, then washed with brine (50 mL), dried (MgSO$_4$), filtered and concentrated in vacuo. The resultant solid was subjected to flash chromatography (Si-PPC, gradient 0% to 30%, DCM in pentane) to afford the title compound as a yellow liquid (0.504 g, 42%). $^1$H NMR (DMSO-d$_6$): 8.08 (1H, t, J=8.3 Hz), 7.44 (1H, d, J=13.2 Hz), 7.28 (1H, d, J=8.5 Hz), 3.65 (1H, m), 2.33 (2H, m), 2.13 (2H, m), 1.99 (1H, m), 1.84 (1H, m).

Step 2: 4-Cyclobutyl-2-fluoroaniline

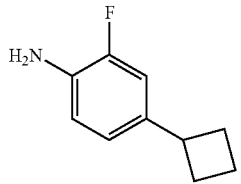

A solution of 4-cyclobutyl-2-fluoro-nitrobenzene (0.5 g, 2.6 mmol) in IMS (5 mL) was degassed with argon for 2 minutes, before 10% Pd/C (0.05 g) was added, and a balloon of hydrogen affixed. The resultant mixture was stirred for 18 hours at room temperature, before being flushed with nitrogen and filtered through hyflo®. The filtrate was concentrated in vacuo to afford the title compound as an orange/red oil (0.31 g, 74%). $^1$H NMR (CDCl$_3$): 6.84 (1H, d, J=12.3 Hz), 6.77 (1H, d, J=8.1 Hz), 6.70 (1H, t, J=9.1 Hz), 3.58 (2H, broad), 3.42 (1H, m), 2.28 (2H, m), 2.01 (3H, m), 1.82 (1H, m).

Step 3: 8-(4-Cyclobutyl-2-fluoro-phenylamino)-imidazo[1,5-a]pyridine-7-carboxylic acid methyl ester

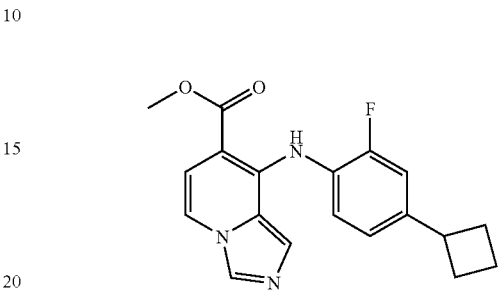

A suspension of 8-chloro-imidazo[1,5-a]pyridine-7-carboxylic acid methyl ester (250 mg, 1.2 mmol), 4-cyclobutyl-2-fluoroaniline (230 mg, 1.4 mmol), Pd$_2$dba$_3$ (43 mg, 0.047 mmol), 2-dicyclohexylphosphino-2',6'-dimethoxy-1,1'-biphenyl (80 mg, 0.19 mmol) and K$_3$PO$_4$ (350 mg, 1.7 mmol) in toluene (5 ml) was degassed with argon for 10 minutes and then heated at 100° C. for 18 hours. The reaction mixture was then cooled to room temperature and filtered through hyflo®. The filtrate was concentrated in vacuo, and the resultant gum was subjected to flash chromatography (Si-PPC, eluting with 5% ethyl acetate in DCM) to afford the title compound as a yellow oil (150 mg, 38%). $^1$H NMR (CDCl$_3$): 7.95 (1H, s), 7.73 (1H, d, J=7.4 Hz), 7.23 (1H, t, J=8.6 Hz), 7.07 (1H, d, J=7.3 Hz), 7.01 (2H, m), 6.50 (1H, s), 3.90 (3H, s), 3.59 (1H, m), 2.39 (2H, m), 2.17 (2H, m), 2.06 (1H, m), 1.93 (1H, m).

Step 4: 8-(4-Cyclobutyl-2-fluoro-phenylamino)-imidazo[1,5-a]pyridine-7-carboxylic acid

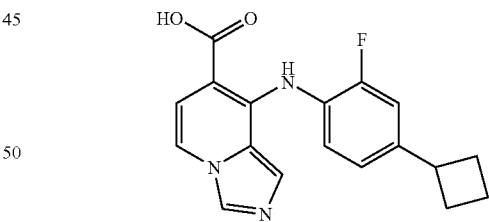

A suspension of 8-(4-cyclobutyl-2-fluoro-phenylamino)-imidazo[1,5-a]pyridine-7-carboxylic acid methyl ester (150 mg, 0.46 mmol) and 1M NaOH (1.5 mL, 1.5 mmol) in IMS (2 mL) was heated at 60° C. for 2 hours. The reaction mixture was then cooled to room temperature, diluted with water and glacial acetic acid was added to adjust pH to 4. The precipitate was filtered off and dried in a drying pistol at 40° C. for 18 hours to afford the title compound as a cream solid (154 mg, 99%). $^1$H NMR (DMSO-d$_6$):10.53 (1 H, s), 8.34 (1 H, s), 7.74 (1 H, d, J=7.3 Hz), 7.35 (1 H, t, J=8.3 Hz), 7.24 (1 H, d, J=11.2 Hz), 7.13(1 H, d, J=8.1 Hz), 7.01 (1H, d, J=9.3 Hz), 6.23 (1H, s), 3.61 (1 H, m), 2.38 (2 H, m), 2.14 (2 H, m), 1.99 (1 H, m), 1.84 (1 H, m).

Step 5: 8-(4-Cyclobutyl-2-fluoro-phenylamino)-imidazo[1,5-a]pyridine-7-carboxylic acid (2-vinyloxy-ethoxy)-amide

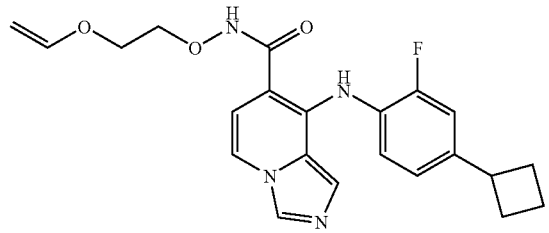

A suspension of 8-(4-cyclobutyl-2-fluoro-phenylamino)-imidazo[1,5-a]pyridine-7-carboxylic acid (154 mg, 0.46 mmol), EDCI (105 mg, 0.55 mmol), HOBt (74 mg, 0.55 mmol), DIPEA (0.19 mL, 1.14 mmol) and O-(2-vinyloxy-ethyl)-hydroxylamine (52 mg, 0.50 mmol) in THF (2.5 mL) was stirred at room temperature for 18 hours. The reaction mixture was partitioned between DCM (20 mL) and saturated aqueous $NaHCO_3$. The organic layer was isolated then washed with water (20 mL), followed by brine (20 mL), dried ($MgSO_4$), filtered and concentrated in vacuo. The resultant gum was subjected to flash chromatography (Si-PPC, gradient 0% to 100%, ethyl actetate in cyclohexane) to afford the title compound as a brown gum (149 mg, 80%). LCMS (method B): $R_T$=3.49 min, $[M+H]^+$=411.

Step 6: 8-(4-Cyclobutyl-2-fluoro-phenylamino)-imidazo[1,5-a]pyridine-7-carboxylic acid (2-hydroxy-ethoxy)-amide 8-(4-Cyclobutyl-2-fluoro-phenylamino)-imidazo[1,5-a]pyridine-7-carboxylic acid (2-vinyloxy-ethoxy)-amide (149 mg, 0.36 mmol) was dissolved in methanol (2 mL) and treated with 1M HCl (1.5 mL). The reaction mixture was stirred at room temperature for 2 hours. The solvents were removed in vacuo and the residue was purified by preparative HPLC (Gemini 5 micron $C_{18}$ 250×21.20 mm column, 0.1% formic acid, gradient acetonitrile/water, 5 to 98%, ramp time 20 minutes) to afford the title compound as a yellow solid (16 mg, 11%). LCMS (method A): $R_T$=7.40 min, $[M+H]^+$=385. $^1$H NMR (DMSO-$d_6$):11.59 (1H, s), 10.60 (1H, s), 8.32 (1H, s), 7.82 (1H, d, J=7.7 Hz), 7.24 (1H, d, J=8.5 Hz), 7.15 (1H, d, J=11.2 Hz), 7.07 (1H, d, J=8.11 Hz), 6.79 (1H, d, J=7.3 Hz), 6.33 (1H, s), 4.73 (1H, s), 3.69 (2H, t, J=4.8 Hz), 3.61 (2H, t, J=5.0 Hz), 3.57 (1H, d, J=8.8 Hz), 2.36 (2H, m), 2.12 (2H, m), 1.96 (1H, m), 1.83 (1H, m).

We claim:

1. A compound of formula I:

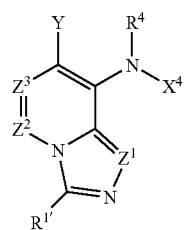

and salts thereof, wherein:

$Z^1$ is $CR^1$;

$R^1$ is H, $C_1$-$C_3$ alkyl, halo, $CF_3$, $CHF_2$, CN, $OR^A$ or $NR^AR^A$;

$R^{1'}$ is H, $C_1$-$C_3$ alkyl, halo, $CF_3$, $CHF_2$, CN, $OR^A$, or $NR^AR^A$;

wherein each $R^A$ is independently H or $C_1$-$C_3$ alkyl;

$Z^2$ is $CR^2$;

$Z^3$ is $CR^3$ $R^2$ and $R^3$ are independently selected from H, halo, CN, $CF_3$, —$OCF_3$, —$NO_2$, —$(CR^{14}R^{15})_nC(=Y')R^{11}$, —$(CR^{14}R^{15})_nC(=Y')OR^{11}$, —$(CR^{14}R^{15})_nC(=Y')NR^{11}R^{12}$, —$(CR^{14}R^{15})_nNR^{11}R^{12}$, —$(CR^{14}R^{15})_nOR^{11}$, —$(CR^{14}R^{15})_nSR^{11}$, —$(CR^{14}R^{15})_nNR^{12}C(=Y')R^{11}$, —$(CR^{14}R^{15})_nNR^{12}C(=Y')OR^{11}$, —$(CR^{14}R^{15})_nNR^{13}C(=Y')NR^{11}R^{12}$, —$(CR^{14}R^{15})_nNR^{12}SO_2R^{11}$, —$(CR^{14}R^{15})_nOC(=Y')R^{11}$, —$(CR^{14}R^{15})_nOC(=Y')OR^{11}$, —$(CR^{14}R^{15})_nOC(=Y')NR^{11}R^{12}$, —$(CR^{14}R^{15})_nOS(O)_2(OR^{11})$, —$(CR^{14}R^{15})_nOP(=Y')(OR^{11})(OR^{12})$, —$(CR^{14}R^{15})_nOP(OR^{11})(OR^{12})$, —$(CR^{14}R^{15})_nS(O)R^{11}$, —$(CR^{14}R^{15})_nS(O)_2R^{11}$, —$(CR^{14}R^{15})_nS(O)_2NR^{11}R^{12}$, —$(CR^{14}R^{15})_nS(O)(OR^{11})$, —$(CR^{14}R^{15})_nS(O)_2(OR^{11})$, —$(CR^{14}R^{15})_nSC(=Y')R^{11}$, —$(CR^{14}R^{15})_nSC(=Y')OR^{11}$, —$(CR^{14}R^{15})_nSC(=Y')NR^{11}R^{12}$, $C_1$-$C_{12}$ alkyl, $C_2$-$C_8$ alkenyl, $C_2$-$C_8$ alkynyl, carbocyclyl, heterocyclyl, aryl, and heteroaryl;

$R^4$ is H, $C_1$-$C_6$ alkyl or $C_3$-$C_4$ carbocyclyl;

Y is W-C(O)- or W';

W is

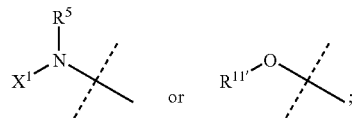

$R^5$ is H or $C_1$-$C_{12}$ alkyl;

$X^1$ is selected from $R^{11'}$ and —$OR^{11'}$; when $X^1$ is $R^{11'}$, $X^1$ is optionally taken together with $R^5$ and the nitrogen atom to which they are bound to form a 4-7 membered saturated or unsaturated ring having 0-2 additional heteroatoms selected from O, S and N, wherein said ring is optionally substituted with one or more groups selected from halo, CN, $CF_3$, —$OCF_3$, —$NO_2$, —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_nSR^{16}$, —$(CR^{19}R^{20})_nNR^{16}C(=Y')R^{17}$, —$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$;

each $R^{11'}$ is independently H, $C_1$-$C_{12}$ alkyl, $C_2$-$C_8$ alkenyl, $C_2$-$C_8$ alkynyl, carbocyclyl, heterocyclyl, aryl, or heteroaryl;

$R^{11}$, $R^{12}$ and $R^{13}$ are independently H, $C_1$-$C_{12}$ alkyl, $C_2$-$C_8$ alkenyl, $C_2$-$C_8$ alkynyl, carbocyclyl, heterocyclyl, aryl, or heteroaryl, or $R^{11}$ and $R^{12}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, CF$_3$, —OCF$_3$, —NO$_2$, C$_1$-C$_6$ alkyl, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

R$^{14}$ and R$^{15}$ are independently selected from H, C$_1$-C$_{12}$ alkyl, aryl, carbocyclyl, heterocyclyl, and heteroaryl;

W' is

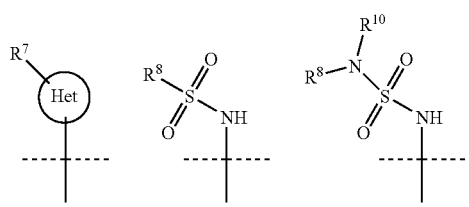

wherein

is

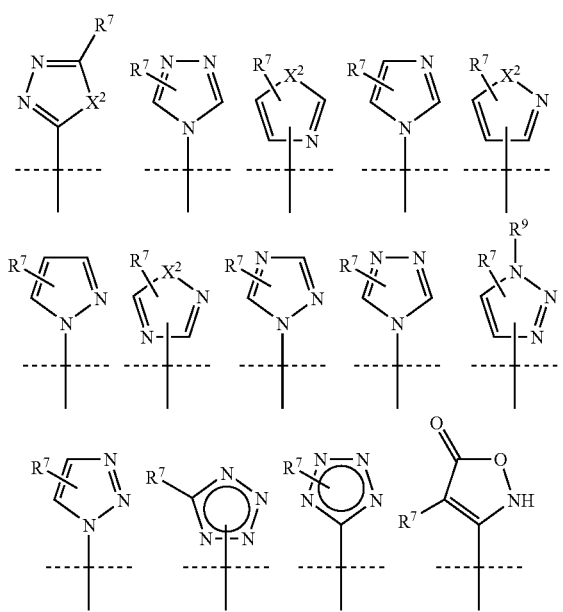

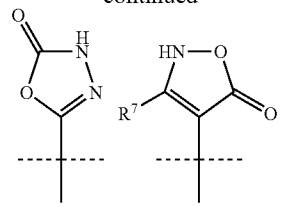

each X$^2$ is independently O, S, or NR$^9$;
each R$^7$ is independently selected from H, halo, CN, CF$_3$, —OCF$_3$, —NO$_2$, —(CR$^{14}$R$^{15}$)$_n$C(=Y')R$^{11}$, —(CR$^{14}$R$^{15}$)$_n$C(=Y')OR$^{11}$, —(CR$^{14}$R$^{15}$)$_n$C(=Y')NR$^{11}$R$^{12}$, —(CR$^{14}$R$^{15}$)$_n$NR$^{11}$R$^{12}$, —(CR$^{14}$R$^{15}$)$_n$OR$^{11}$, —(CR$^{14}$R$^{15}$)$_n$SR$^{11}$, —(CR$^{14}$R$^{15}$)$_n$NR$^{12}$C(=Y')R$^{11}$, —(CR$^{14}$R$^{15}$)$_n$NR$^{12}$C(=Y')OR$^{11}$, —(CR$^{14}$R$^{15}$)$_n$NR$^{13}$C(=Y')NR$^{11}$R$^{12}$, —(CR$^{14}$R$^{15}$)$_n$NR$^{12}$SO$_2$R$^{11}$, —(CR$^{14}$R$^{15}$)$_n$OC(=Y')R$^{11}$, —(CR$^{14}$R$^{15}$)$_n$OC(=Y')OR$^{11}$, —(CR$^{14}$R$^{15}$)$_n$OC(=Y')NR$^{11}$R$^{12}$, —(CR$^{14}$R$^{15}$)$_n$OS(O)$_2$(OR$^{11}$), —(CR$^{14}$R$^{15}$)$_n$S(O)$_2$NR$^{11}$R$^{12}$, —(CR$^{14}$R$^{15}$)$_n$S(O)(OR$^{11}$), —(CR$^{14}$R$^{15}$)$_n$S(O)$_2$(OR$^{11}$), —(CR$^{14}$R$^{15}$)$_n$SC(=Y')R$^{11}$, —(CR$^{14}$R$^{15}$)$_n$SC(=Y')OR$^{11}$, —(CR$^{14}$R$^{15}$)$_n$SC(=Y')NR$^{11}$R$^{12}$, C$_1$-C$_{12}$ alkyl, C$_2$-C$_8$ alkenyl, C$_2$-C$_8$ alkynyl, carbocyclyl, heterocyclyl, aryl, and heteroaryl;

each R$^8$ is independently selected from C$_1$-C$_{12}$ alkyl, aryl, carbocyclyl, heterocyclyl, and heteroaryl;

R$^9$ is selected from H, —(CR$^{14}$R$^{15}$)$_n$C(=Y')R$^{11}$, —(CR$^{14}$R$^{15}$)$_n$C(=Y')OR$^{11}$, —(CR$^{14}$R$^{15}$)$_n$C(=Y')NR$^{11}$R$^{12}$, —(CR$^{14}$R$^{15}$)$_q$NR$^{11}$R$^{12}$, —(CR$^{14}$R$^{15}$)$_q$R$^{11}$, —(CR$^{14}$R$^{15}$)$_q$SR$^{11}$, —(CR$^{14}$R$^{15}$)$_q$NR$^{12}$C(=Y')R$^{11}$, —(CR$^{14}$R$^{15}$)$_q$NR$^{12}$C(=Y')OR$^{11}$, —(CR$^{14}$R$^{15}$)$_q$NR$^{13}$C(=Y')NR$^{11}$R$^{12}$, —(CR$^{14}$R$^{15}$)$_q$NR$^{12}$SO$_2$R$^{11}$, —(CR$^{14}$R$^{15}$)$_q$OC(=Y')R$^{11}$, —(CR$^{14}$R$^{15}$)$_q$OC(=Y')OR$^{11}$, —(CR$^{14}$R$^{15}$)$_q$OC(=Y')NR$^{11}$R$^{12}$, —(CR$^{14}$R$^{15}$)$_q$OS(O)$_2$(OR$^{11}$), —(CR$^{14}$R$^{15}$)$_q$OP(=Y')(OR$^{11}$)(OR$^{12}$), —(CR$^{14}$R$^{15}$)$_q$OP(OR$^{11}$)(OR$^{12}$), —(CR$^{14}$R$^{15}$)$_n$S(O)R$^{11}$, —(CR$^{14}$R$^{15}$)$_n$S(O)$_2$R$^{11}$, —(CR$^{14}$R$^{15}$)$_n$S(O)$_2$NR$^{11}$R$^{12}$, C$_1$-C$_{12}$ alkyl, C$_2$-C$_8$ alkenyl, C$_2$-C$_8$ alkynyl, carbocyclyl, heterocyclyl, aryl, and heteroaryl;

R$^{10}$ is H, C$_1$-C$_6$ alkyl or C$_3$-C$_4$ carbocyclyl;

X$^4$ is

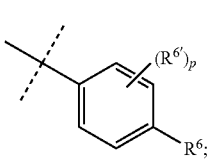

R$^6$ is H, halo, C$_1$-C$_6$ alkyl, C$_2$-C$_8$ alkenyl, C$_2$-C$_8$ alkynyl, carbocyclyl, heteroaryl, heterocyclyl, —OCF$_3$, —NO$_2$, —Si(C$_1$-C$_6$ alkyl), —(CR$^{19}$R$^{20}$)$_n$NR$^{16}$R$^{17}$, —(CR$^{19}$R$^{20}$)$_n$OR$^{16}$, or —(CR$^{19}$R$^{20}$)$_n$SR$^{16}$;

R$^{6'}$ is H, halo, C$_1$-C$_6$ alkyl, carbocyclyl, CF$_3$, —OCF$_3$, —NO$_2$, —Si(C$_1$-C$_6$ alkyl), —(CR$^{19}$R$^{20}$)$_n$NR$^{16}$R$^{17}$, —(CR$^{19}$R$^{20}$)$_n$SR$^{16}$, —(CR$^{19}$R$^{20}$)$_n$—SR$^{16}$, C$_2$-C$_8$ alkenyl, C$_2$-C$_8$ alkynyl, heterocyclyl, aryl, or heteroaryl;

p is 0, 1, 2 or 3;
n is 0, 1, 2 or 3;
q is 2 or 3;

wherein each said alkyl, alkenyl, alkynyl, carbocyclyl, heterocyclyl, aryl and heteroaryl of R$^1$, R$^2$, R$^3$, R$^4$, R$^5$, R$^6$, R$^{6'}$, R$^7$, R$^8$, R$^9$, R$^{10}$, R$^{11}$, R$^{11'}$, R$^{12}$, R$^{13}$, R$^{14}$, R$^{15}$ and R$^A$ is independently optionally substituted with one or more groups independently selected from halo, CN, CF$_3$, —OCF$_3$, —NO$_2$, oxo, —Si(C$_1$-C$_6$ alkyl), —(CR$^{19}$R$^{20}$)$_n$C(=Y')R$^{16}$, —(CR$^{19}$R$^{20}$)$_n$C(=Y')OR$^{16}$, —(CR$^{19}$R$^{20}$)$_n$C(=Y')NR$^{16}$R$^{17}$, —(CR$^{19}$R$^{20}$)$_n$NR$^{16}$R$^{17}$, —(CR$^{19}$R$^{20}$)$_n$OR$^{16}$, —(CR$^{19}$R$^{20}$)$_n$SR$^{16}$, —(CR$^{19}$R$^{20}$)$_n$NR$^{16}$C(=Y')R$^{17}$, —(CR$^{19}$R$^{20}$)$_n$NR$^{16}$C(=Y')OR$^{17}$, —(CR$^{19}$R$^{20}$)$_n$NR$^{18}$C(=Y')NR$^{16}$R$^{17}$, —(CR$^{19}$R$^{20}$)$_n$NR$^{17}$SO$_2$R$^{16}$, —(CR$^{19}$R$^{20}$)$_n$OC(=Y')R$^{16}$), —(CR$^{19}$R$^{20}$)$_n$OC(=Y')OR$^{16}$, —(CR$^{19}$R$^{20}$)$_n$OC(=Y')NR$^{16}$R$^{17}$, —(CR$^{19}$R$^{20}$)$_n$OS(O)$_2$(OR$^{16}$), —(CR$^{19}$R$^{20}$)$_n$OP(=Y')(OR$^{16}$)(OR$^{17}$), —(CR$^{19}$R$^{20}$)$_n$OP(OR$^{16}$)(OR$^{17}$), —(CR$^{19}$R$^{20}$)$_n$S(O)R$^{16}$, —(CR$^{19}$R$^{20}$)$_n$S(O)$_2$R$^{16}$, —(CR$^{19}$R$^{20}$)$_n$S(O)$_2$NR$^{16}$R$^{17}$, —(CR$^{19}$R$^{20}$)$_n$S(O)(OR$^{16}$), —(CR$^{19}$R$^{20}$)$_n$S(O)$_2$(OR$^{16}$), —(CR$^{19}$R$^{20}$)$_n$SC(=Y')R$^{16}$, —(CR$^{19}$R$^{20}$)$_n$SC(=Y')OR$^{16}$), —(CR$^{19}$R$^{20}$)$_n$SC(=Y')NR$^{16}$R$^{17}$, and R$^{21}$;

each R$^{16}$, R$^{17}$ and R$^{18}$ is independently H, C$_1$-C$_{12}$ alkyl, C$_2$-C$_8$ alkenyl, C$_2$-C$_8$ alkynyl, carbocyclyl, heterocyclyl, aryl, or heteroaryl, wherein said alkyl, alkenyl, alkynyl, carbocyclyl, heterocyclyl, aryl, or heteroaryl is optionally substituted with one or more groups selected from halo, CN, —OCF$_3$, CF$_3$, —NO$_2$, C$_1$-C$_6$ alkyl, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

or R$^{16}$ and R$^{17}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, —OCF$_3$, CF$_3$, —NO$_2$, C$_1$-C$_6$ alkyl, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

R$^{19}$ and R$^{20}$ are independently selected from H, C$_1$-C$_{12}$ alkyl, —(CH$_2$)$_n$-aryl, —(CH$_2$)$_n$-carbocyclyl, —(CH$_2$)$_n$-heterocyclyl, and —(CH$_2$)$_n$-heteroaryl;

R$^{21}$ is C$_1$-C$_{12}$ alkyl, C$_2$-C$_8$ alkenyl, C$_2$-C$_8$ alkynyl, carbocyclyl, heterocyclyl, aryl, or heteroaryl, wherein each member of R$^{21}$ is optionally substituted with one or more groups selected from halo, oxo, CN, —OCF$_3$, CF$_3$, —NO$_2$, C$_1$-C$_6$ alkyl, —OH, —SH, —O(C$_1$-C$_6$ alkyl), —S(C$_1$-C$_6$ alkyl), —NH$_2$, —NH(C$_1$-C$_6$ alkyl), —N(C$_1$-C$_6$ alkyl)$_2$, —SO$_2$(C$_1$-C$_6$ alkyl), —CO$_2$H, —CO$_2$(C$_1$-C$_6$ alkyl), —C(O)NH$_2$, —C(O)NH(C$_1$-C$_6$ alkyl), —C(O)N(C$_1$-C$_6$ alkyl)$_2$, —N(C$_1$-C$_6$ alkyl)C(O)(C$_1$-C$_6$ alkyl), —NHC(O)(C$_1$-C$_6$ alkyl), —NHSO$_2$(C$_1$-C$_6$ alkyl), —N(C$_1$-C$_6$ alkyl)SO$_2$(C$_1$-C$_6$ alkyl), —SO$_2$NH$_2$, —SO$_2$NH(C$_1$-C$_6$ alkyl), —SO$_2$N(C$_1$-C$_6$ alkyl)$_2$, —OC(O)NH$_2$, —OC(O)NH(C$_1$-C$_6$ alkyl), —OC(O)N(C$_1$-C$_6$ alkyl)$_2$, —OC(O)O(C$_1$-C$_6$ alkyl), —NHC(O)NH(C$_1$-C$_6$ alkyl), —NHC(O)N(C$_1$-C$_6$ alkyl)$_2$, —N(C$_1$-C$_6$ alkyl)C(O)NH(C$_1$-C$_6$ alkyl), —N(C$_1$-C$_6$ alkyl)C(O)N(C$_1$-C$_6$ alkyl)$_2$, —NHC(O)NH(C$_1$-C$_6$ alkyl), —NHC(O)N(C$_1$-C$_6$ alkyl)$_2$, —NHC(O)O(C$_1$-C$_6$ alkyl), and —N(C$_1$-C$_6$ alkyl)C(O)O(C$_1$-C$_6$ alkyl);

each Y' is independently O, NR$^{22}$, or S; and

R$^{22}$ is H or C$_1$-C$_{12}$ alkyl.

2. The compound of claim 1 wherein R$^2$ is H, methyl, CF$_3$, Cl, F.

3. The compound of claim 2 wherein R$^2$ is H, Cl or F.

4. The compound of claim 1 wherein R$^3$ is H, methyl, CF$_3$, Cl, F.

5. The compound of claim 4 wherein R$^3$ is H, Cl or F.

6. The compound of claim 1 wherein R$^1$ is H or methyl.

7. The compound of claim 6 wherein R$^1$ is H.

8. The compound of claim 6 wherein R$^{1'}$ is H.

9. The compound of claim 8 wherein Y is W-C(O), W is X$^1$-N(R$^5$)-, and X$^1$ is selected from:

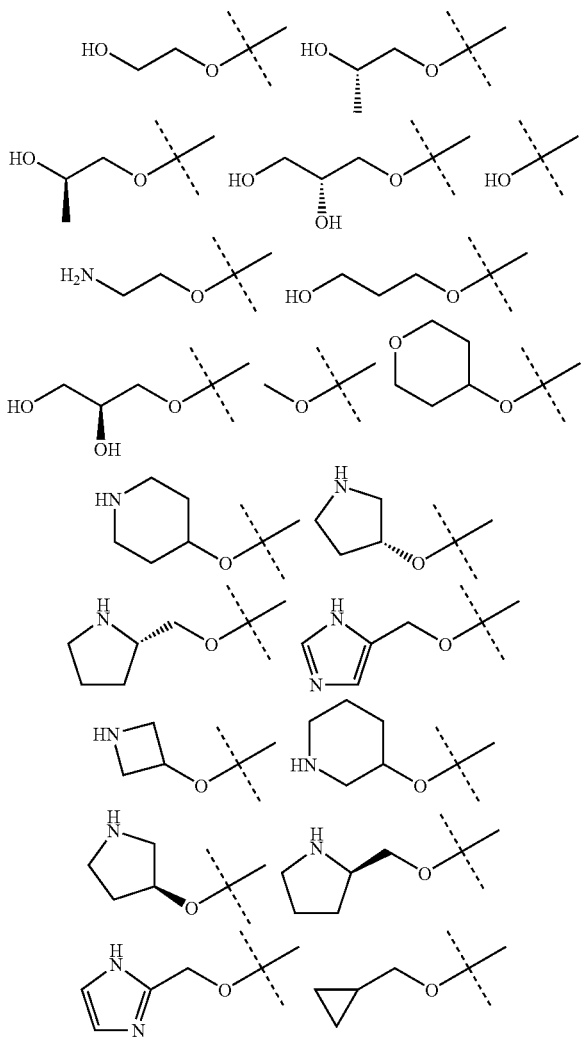

-continued
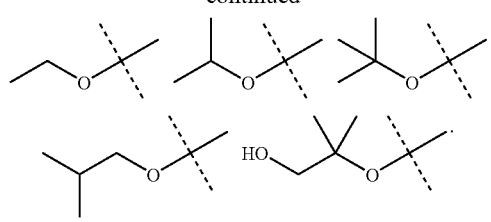
10. The compound of claim 8 wherein Y is W-C(O), W is $X^1$-N($R^5$)-, and $X^1$ is selected from:
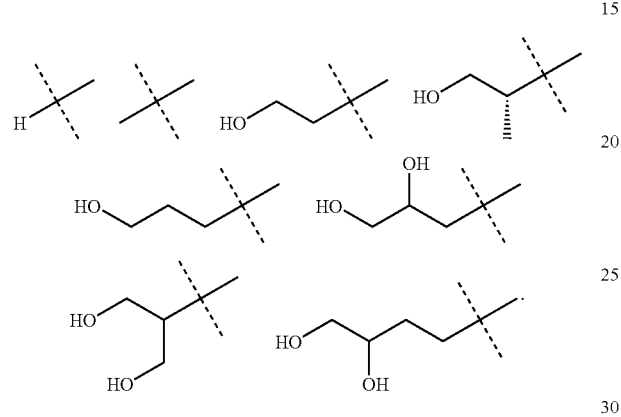
11. The compound of claim 10 wherein $X^4$ is selected from:
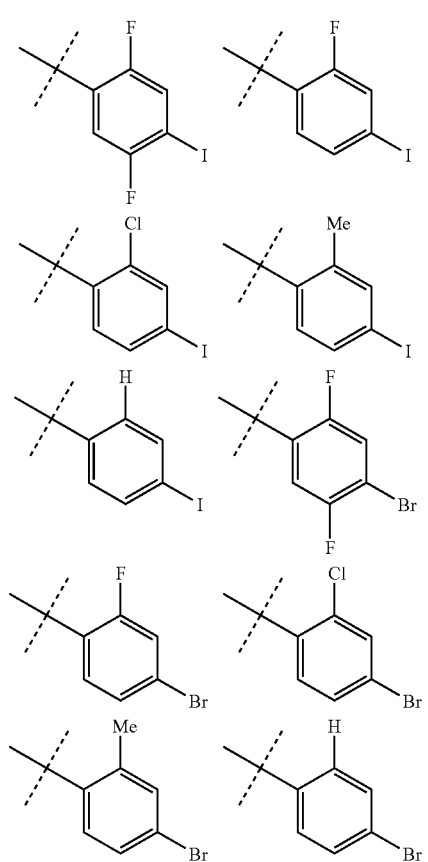
-continued
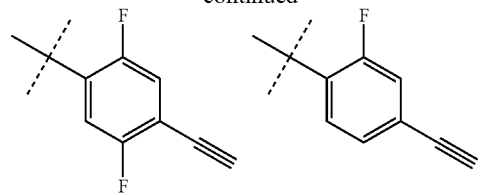
12. The compound of claim 11 wherein $R^4$ is H or methyl.
13. The compound of claim 12 wherein $R^4$ is H.
14. The compound of claim 12 wherein $R^5$ is H or methyl.
15. The compound of claim 14 wherein $R^5$ is H.

16. The compound of claim 1 wherein the compound is selected from the group consisting of:

- 8-(4-cyclopropyl-2-fluoro-phenylamino)-imidazo[1,5-a]pyridine-7-carboxylic acid amide;
- 8-(4-cyclopropyl-2-fluoro-phenylamino)-imidazo[1,5-a]pyridine-7-carboxylic acid (2-hydroxy-ethoxy)-amide;
- 8-(2-fluoro-4-methylsulfanyl-phenylamino)-imidazo[1,5-a]pyridine-7-carboxylic acid (2-hydroxy-ethoxy)-amide;
- 8-(2-fluoro-4-iodo-phenylamino)-imidazo[1,5-a]pyridine-7-carboxylic acid (2-hydroxy-ethoxy)-amide;
- 8-(4-cyclopropyl-2-fluoro-phenylamino)-imidazo[1,5-a]pyridine-7-carboxylic acid ((S)-2-hydroxy-propoxy)-amide;
- 8-(4-cyclopropyl-2-fluoro-phenylamino)-imidazo[1,5-a]pyridine-7-carboxylic acid (2-hydroxy-1,1-dimethyl-ethoxy)-amide;
- 8-(4-bromo-2-fluoro-phenylamino)-imidazo[1,5-a]pyridine-7-carboxylic acid (2-hydroxy-ethoxy)-amide;
- 8-(4-bromo-2-fluoro-phenylamino)-imidazo[1,5-a]pyridine-7-carboxylic acid ((S)-2-hydroxy-propoxy)-amide;
- 8-(4-Bromo-2-chloro-phenylamino)-imidazo[1,5-a]pyridine-7-carboxylic acid (2-hydroxy-ethoxy)-amide; and,
- 8-(4-Bromo-2-chloro-phenylamino)-imidazo[1,5-a]pyridine-7-carboxylic acid (2-hydroxy-ethoxy)-amide.

17. A pharmaceutical composition comprising a compound of any one of claim 1, and a pharmaceutically acceptable carrier.

* * * * *

UNITED STATES PATENT AND TRADEMARK OFFICE
CERTIFICATE OF CORRECTION

PATENT NO. : 8,293,763 B2
APPLICATION NO. : 12/808346
DATED : October 23, 2012
INVENTOR(S) : Price et al.

Page 1 of 1

It is certified that error appears in the above-identified patent and that said Letters Patent is hereby corrected as shown below:

Under Column 66, line 21, after "$OS(O)_2(OR^{11})$,", please insert

-- $-(CR^{14}R^{15})_nOP(=Y')(OR^{11})(OR^{12})$, $-(CR^{14}R^{15})_nOP(OR^{11})(OR^{12})$, $-(CR^{14}R^{15})_nS(O)R^{11}$, $-(CR^{14}R^{15})_nS(O)_2R^{11}$, --; and on line 31, please delete "$-(CR^{14}R^{15})_qR^{11}$, and insert -- $-(CR^{14}R^{15})_qOR^{11}$ --.

Signed and Sealed this
Fourth Day of December, 2012

David J. Kappos
*Director of the United States Patent and Trademark Office*